(12) United States Patent
Huang et al.

(10) Patent No.: US 11,786,609 B2
(45) Date of Patent: Oct. 17, 2023

(54) LIPID COMPOUND AS WELL AS LIPID VECTOR, NUCLEIC ACID LIPID NANOPARTICLE COMPOSITION, AND PHARMACEUTICAL PREPARATION COMPRISING THE SAME

(71) Applicant: PURECODON (HONG KONG) BIOPHARMA LIMITED, Hong Kong (CN)

(72) Inventors: Ke Huang, Suzhou (CN); Chaoxuan Jing, Suzhou (CN); Yingwen Li, Suzhou (CN); Yinjia Gao, Suzhou (CN); Yuping Liu, Suzhou (CN); Zhenhua Sun, Suzhou (CN)

(73) Assignee: PURECODON (HONG KONG) BIOPHARMA LIMITED, Hong Kong (CN)

( * ) Notice: Subject to any disclaimer, the term of this patent is extended or adjusted under 35 U.S.C. 154(b) by 0 days.

(21) Appl. No.: 17/873,404

(22) Filed: Jul. 26, 2022

(65) Prior Publication Data

US 2022/0378938 A1    Dec. 1, 2022

Related U.S. Application Data

(63) Continuation of application No. PCT/CN2022/080352, filed on Mar. 11, 2022.

(30) Foreign Application Priority Data

Apr. 30, 2021  (CN) .......................... 202110483495.8
Jun. 15, 2021  (CN) .......................... 202110662426.3

(51) Int. Cl.
*A61K 9/127*  (2006.01)
*A61K 9/51*   (2006.01)
(Continued)

(52) U.S. Cl.
CPC ............ *A61K 48/005* (2013.01); *A61K 9/127* (2013.01); *A61K 9/5123* (2013.01);
(Continued)

(58) Field of Classification Search
CPC .............................. A61K 9/127; C07C 219/06
See application file for complete search history.

(56) References Cited

U.S. PATENT DOCUMENTS 10,675,251 B2   6/2020  Rannard et al.
2011/0117125 A1*  5/2011  Hope ..................... C07C 219/08
                                              424/234.1
(Continued)

FOREIGN PATENT DOCUMENTS

CN     1208353 A      2/1999
CN   108033895 A      5/2018
(Continued)

OTHER PUBLICATIONS

Stephen M. Berge, Lyle D. Bighley, and Donald C. Monkhouse. "Pharmaceutical Salts." Journal of Pharmaceutical Sciences, vol. 66 No. 1, Jan. 1977, pp. 1-19. (Year: 1977).*

(Continued)

*Primary Examiner* — Isaac Shomer
(74) *Attorney, Agent, or Firm* — Fish & Richardson P.C.

(57) ABSTRACT

The present disclosure belongs to the technical field of gene therapy, and specifically relates to a series of lipid compounds as well as lipid vectors, nucleic acid lipid nanoparticle compositions, and pharmaceutical preparations containing the same. The compound having the structure of formula (I) provided by the present disclosure may be used in combination with other lipid compounds to prepare a lipid vector, which exhibits pH responsiveness, has high encapsulation efficiency for nucleic acid drugs, and greatly (Continued)

enhances the in-vivo delivery efficiency of nucleic acid drugs. Moreover, it is possible to select lipid compounds with different structures as lipid vectors to adjust the enrichment of nucleic acid drugs in different organs, thereby having good market application prospect.

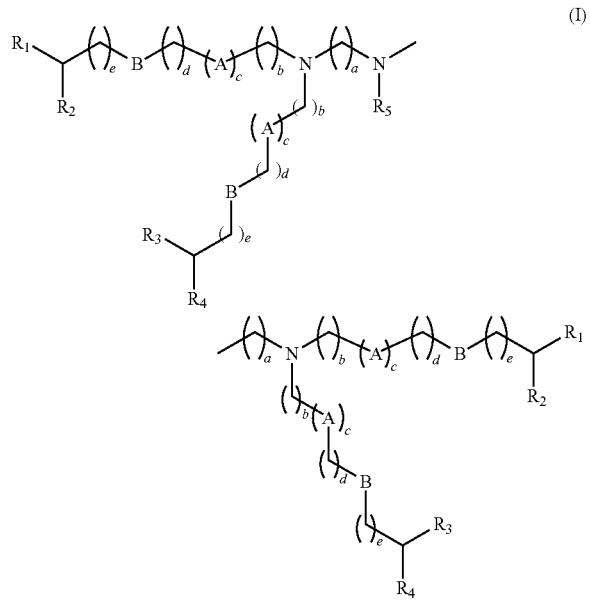

(I)

16 Claims, 4 Drawing Sheets

(51) Int. Cl.

| | | |
|---|---|---|
| *C07C 219/06* | (2006.01) | |
| *C07C 291/00* | (2006.01) | |
| *C07C 323/52* | (2006.01) | |
| *C07C 327/06* | (2006.01) | |
| *C12N 15/88* | (2006.01) | |
| *A61K 48/00* | (2006.01) | |

(52) U.S. Cl.
CPC ........ *A61K 48/0033* (2013.01); *C07C 219/06* (2013.01); *C07C 291/00* (2013.01); *C07C 323/52* (2013.01); *C07C 327/06* (2013.01); *C12N 15/88* (2013.01)

(56) References Cited

U.S. PATENT DOCUMENTS

| | | | |
|---|---|---|---|
| 2016/0114042 A1 | 4/2016 | Anderson et al. | |
| 2018/0155304 A1* | 6/2018 | Nakai | A61K 31/713 |
| 2018/0311176 A1* | 11/2018 | Ozsolak | A61K 9/5153 |
| 2019/0351048 A1* | 11/2019 | Rauch | C12N 15/86 |
| 2020/0129445 A1* | 4/2020 | Patel | A61K 9/08 |
| 2021/0122702 A1* | 4/2021 | Du | A61K 47/24 |

FOREIGN PATENT DOCUMENTS

| | | | | |
|---|---|---|---|---|
| CN | 111954542 A | 11/2020 | | |
| CN | 113402404 A | 9/2021 | | |
| WO | WO 19972026921 | 7/1997 | | |
| WO | WO 2014028487 A1 | 2/2014 | | |
| WO | WO 2019036028 A1 | 2/2019 | | |
| WO | WO 2019089828 A1 | 5/2019 | | |
| WO | WO 2019152848 | 8/2019 | | |
| WO | WO-2020051220 A1 * | 3/2020 | ......... A61K 31/7105 | |
| WO | WO 2020247604 A1 | 12/2020 | | |
| WO | WO-2021030701 A1 * | 2/2021 | ........... A61K 9/0019 | |
| WO | WO 2021030701 A1 | 2/2021 | | |

OTHER PUBLICATIONS

Akinc, "A combinatorial library of lipid-like materials for delivery of RNAi therapeutics," Nature Biotechnology, Apr. 27, 2008, 26(5):561-569.

CN Office Action in Chinese Appln. No. 202110662426.3, dated Dec. 21, 2021, 14 pages (with English Translation).

Hajj et al., "Branched-Tail Lipid Nanoparticles Potently Deliver mRNA In Vivo due to Enhanced Ionization at Endosomal pH," Small, Jan. 13, 2019, 15(6):1805097, pp. 1-7.

PCT International Search Report in International Appln. No. PCT/CN2022/080352, dated May 25, 2022, 10 pages (No. Translation).

* cited by examiner

LIPID COMPOUND AS WELL AS LIPID VECTOR, NUCLEIC ACID LIPID NANOPARTICLE COMPOSITION, AND PHARMACEUTICAL PREPARATION COMPRISING THE SAME

CROSS-REFERENCE TO RELATED APPLICATION

Pursuant to 35 U.S.C § 119(e), this application is a continuation of International Application No. PCT/CN2022/080352, filed on Mar. 11, 2022, which claims priority to and the benefit of Chinese Patent Applications No. 202110483495.8, filed on Apr. 30, 2021, and No. 202110662426.3, filed on Jun. 15, 2021. All the aforementioned documents are incorporated herein by reference.

TECHNICAL FIELD

The present disclosure belongs to the technical field of gene therapy, and specifically relates to a lipid compound as well as a lipid vector, a nucleic acid lipid nanoparticle composition, and a pharmaceutical preparation comprising the same.

BACKGROUND

Gene therapy technology is a research focus in the field of modern biomedicine, and the utilization of nucleic acid drugs may prevent cancers and bacterial and viral infections as well as treating diseases with genetic pathogenesis, etc. Since nucleic acid drugs have characteristics such as easiness in degradation and difficulty in entering cells, there is a need to encapsulate nucleic acid drugs with the help of vectors and deliver the same to target cells. Therefore, the development of safe and efficient delivery vectors has become a prerequisite for the clinical application of gene therapy.

Lipid nanoparticle (LNP) is currently a research focus in the field of non-viral gene vectors. In 2018, the FDA approved LNP-delivered patisiran (onpattro) for treating hereditary transthyretin amyloidosis. Since then, researches that utilize LNP technology to deliver nucleic acid drugs have shown a burst of increase. Especially, at the end of 2020, FDA approved two vaccines against the novel coronavirus COVID-19, which are respectively produced by Moderna and BioNtech & Pfizer. Both vaccines utilize LNP technology to deliver mRNA drugs, thus realizing the prevention against COVID-19 virus.

LNP usually consists of four lipid compounds, that is, a cationic lipid, a neutral lipid, a sterol, and an amphiphilic lipid. Among them, the selection of cationic lipid exerts the greatest impact on LNP, for example, influencing the encapsulation efficiency of the nucleic acid drug, the in-vivo delivery efficiency of the nucleic acid drug, cytotoxicity, and the like.

In view of this, it will be of great significance to develop a novel compound that may be used as a cationic lipid.

SUMMARY

Problems to be Solved by the Present Disclosure

The present disclosure aims to provide a series of compounds, which may be used in combination with other lipid compounds to prepare lipid vectors, thereby enhancing the in-vivo delivery efficiency of the nucleic acid drug. It is possible to select lipid compounds with different structures as lipid vectors to adjust the enrichment of the nucleic acid drug in different organs.

The present disclosure also provides a lipid vector comprising the above-mentioned compound.

The present disclosure also provides a nucleic acid lipid nanoparticle composition comprising the above-mentioned compound or the above-mentioned lipid vector.

The present disclosure also provides a pharmaceutical preparation comprising the above-mentioned compound, or the above-mentioned lipid vector, or the above-mentioned nucleic acid lipid nanoparticle composition.

Means for Solving the Problems

<First Aspect>

The present disclosure provides a compound of formula (I), or a pharmaceutically acceptable salt, a stereoisomer, a tautomer, a solvate, a chelate, a non-covalent complex or a prodrug thereof, $$R_1\underset{R_2}{\diagdown}(\phantom{a})_e B(\phantom{a})_d(A)_c(\phantom{a})_b N(\phantom{a})_a N(\phantom{a})_a N(\phantom{a})_b (A)_c(\phantom{a})_d B(\phantom{a})_e\underset{R_2}{\diagup} R_1,$$

(I)

wherein each of A and B is independently one or more substituents selected from the group consisting of —O(C=O)—, —(C=O)O—, —C(=O)—, —O—, —S(O)—, —S—S—, —C(=O)S—, —SC(=O)—, —NR$^a$C(=O)—, —C(=O)NR$^a$—, —NR$^a$OC(=O)—, —OC(=O)NR$^a$—, —NR$^a$OC(=O)NR$^a$—, —NR$^a$C(=O)NR$^a$—, and —NR$^a$C(=O)O—;

each of $R_1$, $R_2$, $R_3$ and $R_4$ is independently hydrogen or an alkyl group containing 1 to 16 carbon atoms, the alkyl group is optionally interrupted with at least one W, and each W is independently one or more substituents selected from the group consisting of —O(C=O)—, —(C=O)O—, —S—S—, —CH=CH—, —C(=O)—, —O—, —S(O)—, —C(=O)S—, —NR$^a$C(=O)—, —NR$^a$C(=O)NR$^a$—, —C(=O)NR$^a$—, —NR$^a$OC(=O)—, —OC(=O)NR$^a$—, and —NR$^a$OC(=O)NR$^a$—;

$R_5$ is hydrogen, a $C_{1-12}$ alkyl group, or a $C_{1-12}$ alkyl group substituted with a hydroxyl group at the end;

each $R^a$ is independently hydrogen or a hydrocarbyl group containing 1 to 24 carbon atoms;

each of a, b, d and e is independently any integer ranging from 0 to 14;

each c is independently 0 or 1;

preferably, in the compound of formula (I), each of A and B is independently one or more substituents selected from the group consisting of —O(C=O)—, —(C=O)O—, —C(=O)—, —O—, —S(O)—, —S—S—, —C(=O)S—, —SC(=O)—, —NHC(=O)—, —C(=O)NH—, —NHC(=O)NH—, —OC(=O)NH—, and —NHC(=O)O—;

each of $R_1$, $R_2$, $R_3$ and $R_4$ is independently hydrogen or an alkyl group containing 1 to 16 carbon atoms, the alkyl group is optionally interrupted with at least one W, and each W is independently one or more substituents selected from the group consisting of —O(C=O)—, —(C=O)O—, —S—S—, —CH=CH—, —C(=O)—, —O—, —S(O)—, —C(=O)S—, —NHC(=O)—, —NHC(=O)NH—, and —OC(=O)NH—;

$R_5$ is hydrogen, a $C_{1-12}$ alkyl group, or a $C_{1-12}$ alkyl group substituted with a hydroxyl group at the end;

each of a, b, d and e is independently any integer ranging from 0 to 14;

each c is independently 0 or 1.

Preferably, the compound has a structure as represented by formula (I-1),

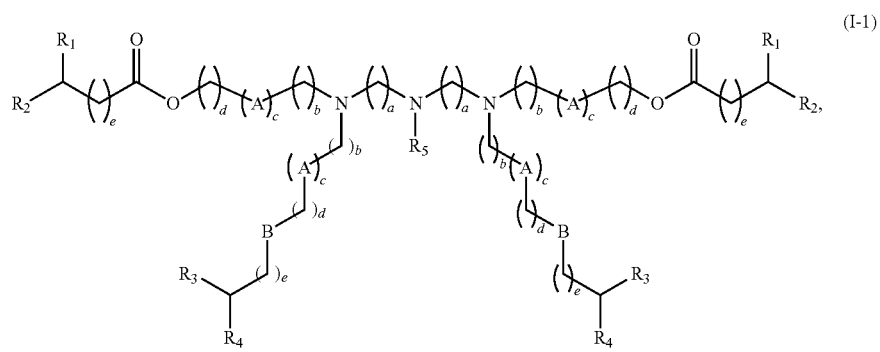

(I-1)

wherein A, B, $R_1$, $R_2$, $R_3$, $R_4$, $R_5$, a, b, c, d and e are as defined in formula (I).

Further preferably, the compound has a structure as represented by formula (I-1-1),

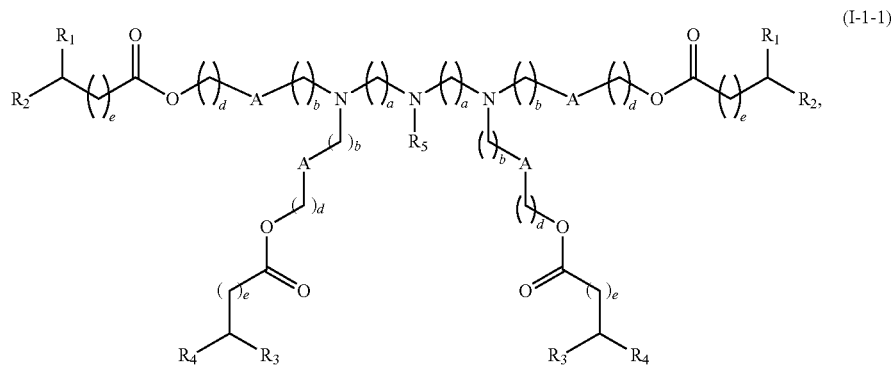

(I-1-1)

wherein A, $R_1$, $R_2$, $R_3$, $R_4$, $R_5$, a, b, d and e are as defined in formula (I-1);

Still further preferably, $R_5$ is a $C_{1-12}$ alkyl group.

Further preferably, the compound has a structure as represented by formula (I-1-2),

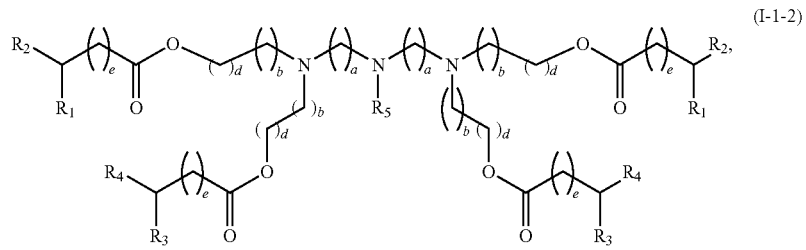
(I-1-2)

wherein $R_1$, $R_2$, $R_3$, $R_4$, $R_5$, a, b, d and e are as defined in formula (I-1);

Still further preferably, the compound has a structure as represented by formula (I-1-2-1),

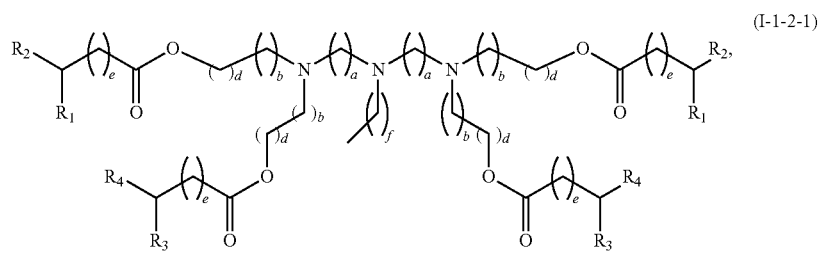
(I-1-2-1)

wherein $R_1$, $R_2$, $R_3$, $R_4$, a, b, d and e are as defined in formula (I-1-2), f is 0 or 1;

Still further preferably, the compound has a structure as represented by formula (I-1-2-2),

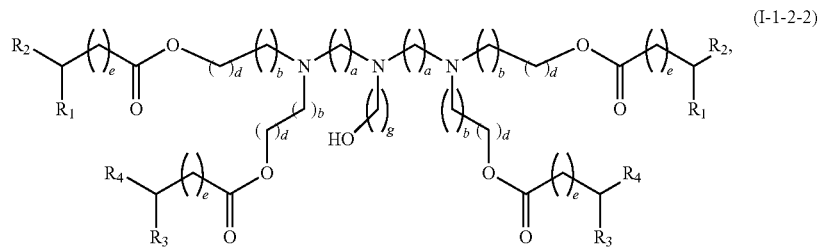
(I-1-2-2)

wherein $R_1$, $R_2$, $R_3$, $R_4$, a, b, d and e are as defined in formula (I-1-2), g is 3 or 4.

Preferably, the compound has a structure as represented by formula (I-2),

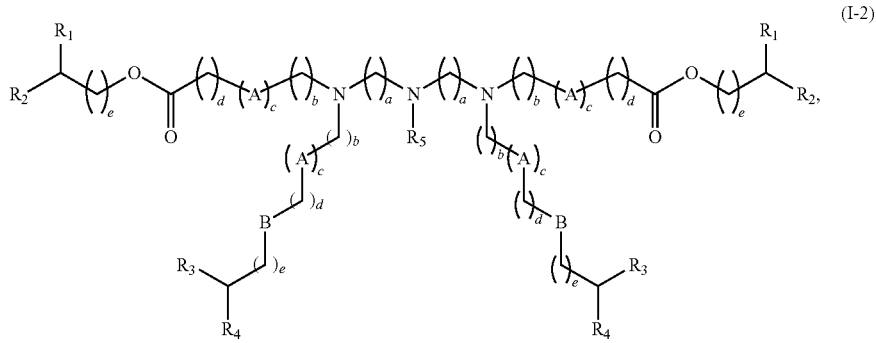

(I-2)

wherein A, B, $R_1$, $R_2$, $R_3$, $R_4$, $R_5$, a, b, c, d and e are as defined in formula (I);

preferably, e is 0 or 1.

<Second Aspect>

The present disclosure provides the following compounds, or pharmaceutically acceptable salts, stereoisomers, tautomers, solvates, chelates, non-covalent complexes or prodrugs thereof,

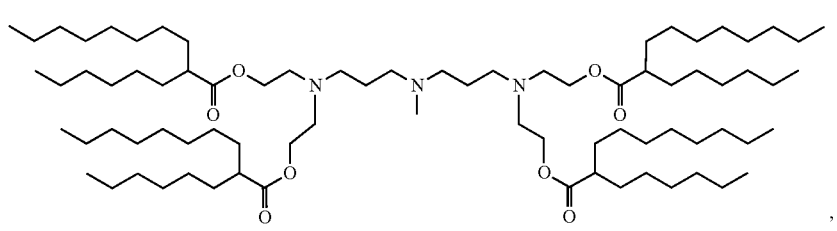

1

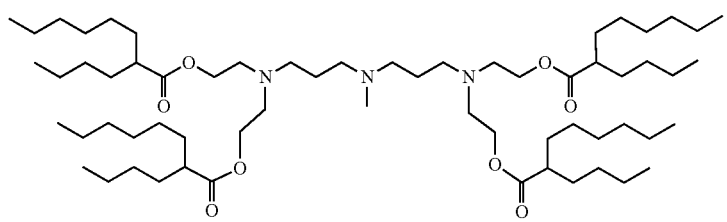

2

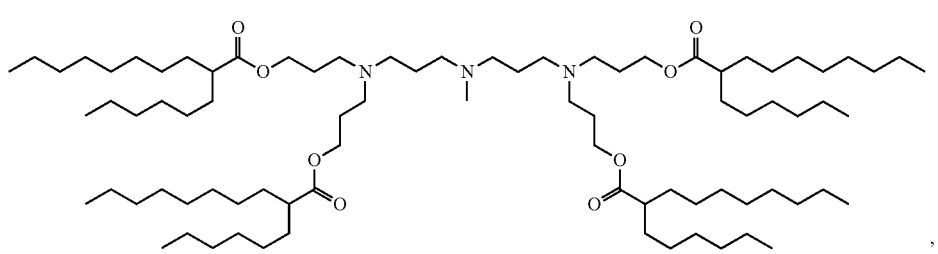

3

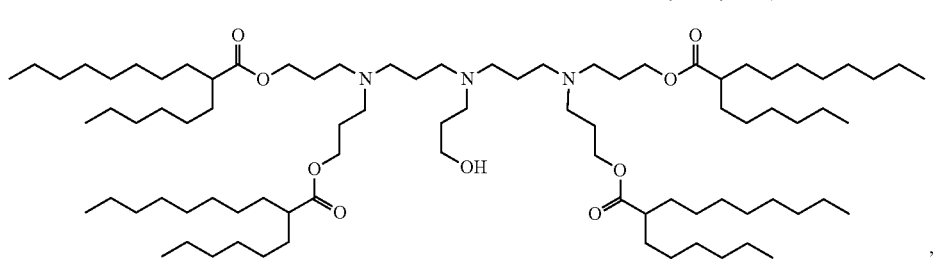

4

5
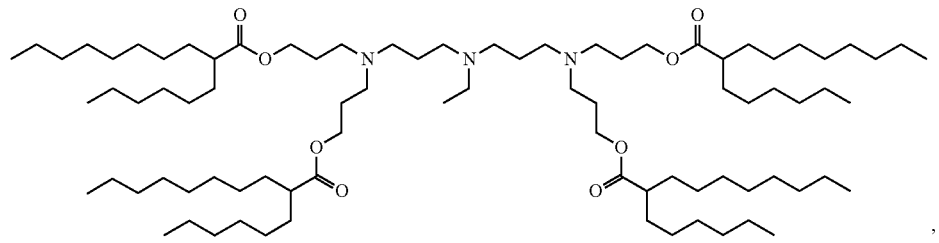
,
6
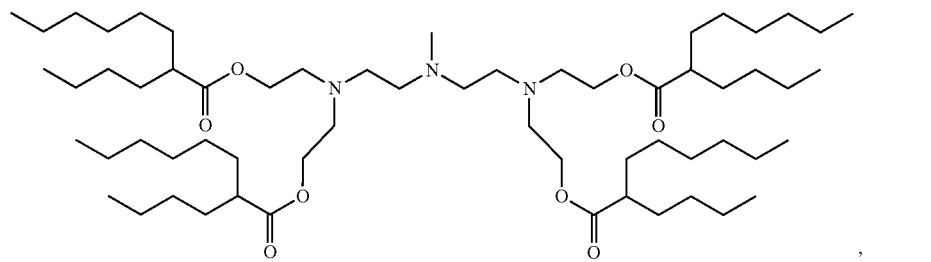
,
7
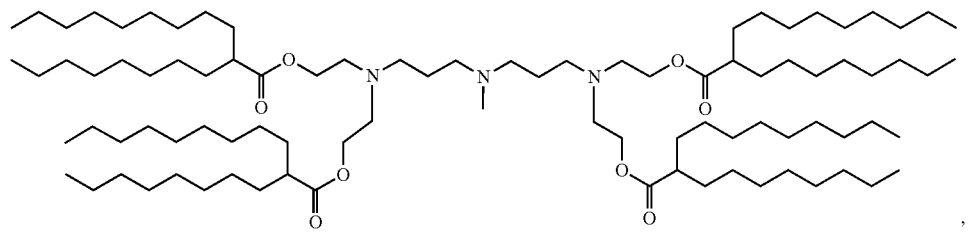
,
8
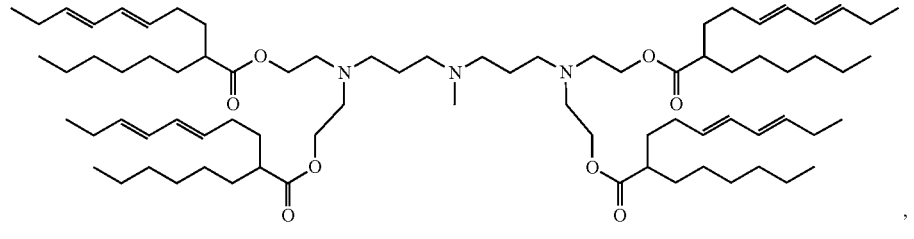
,
9
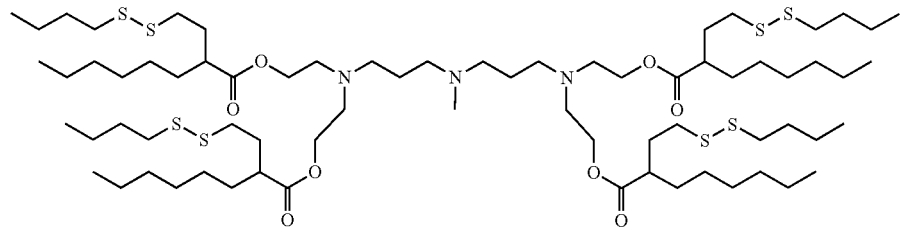
,
10
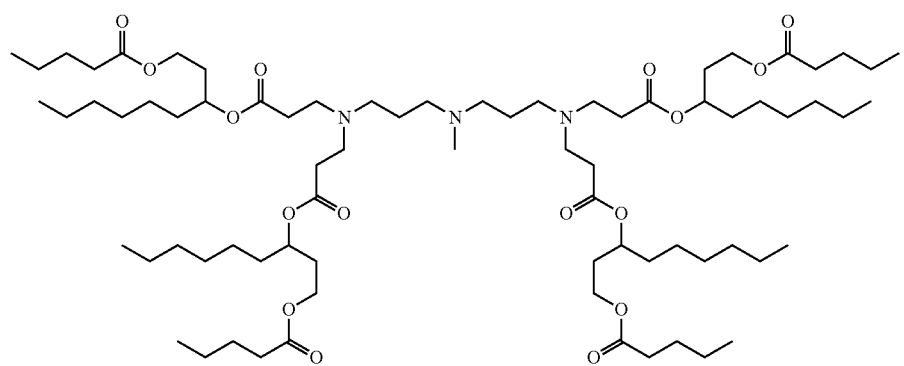
, -continued
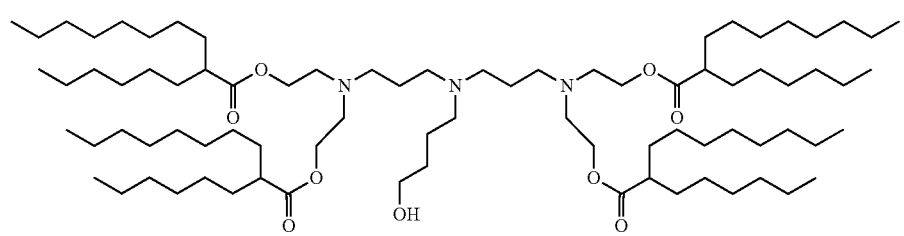
11
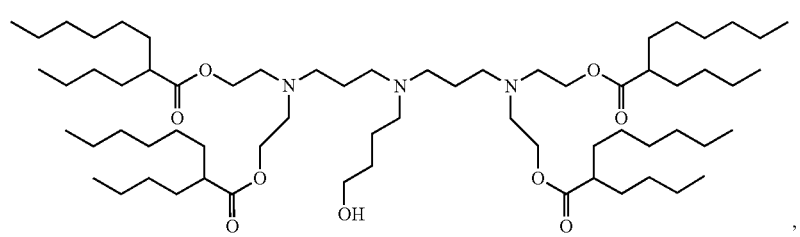
12
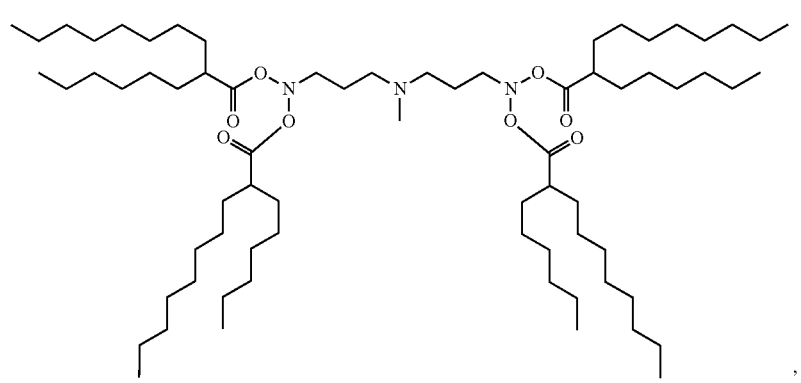
13
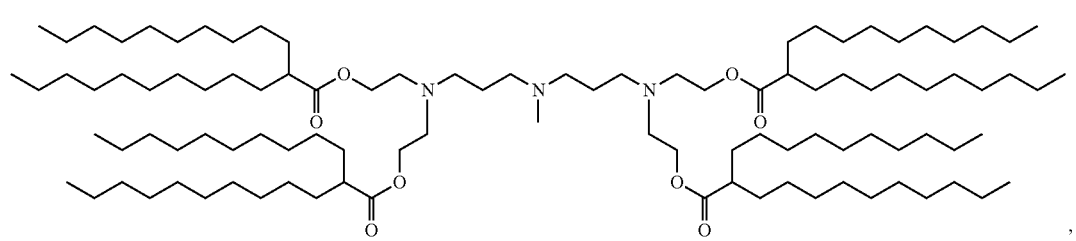
14
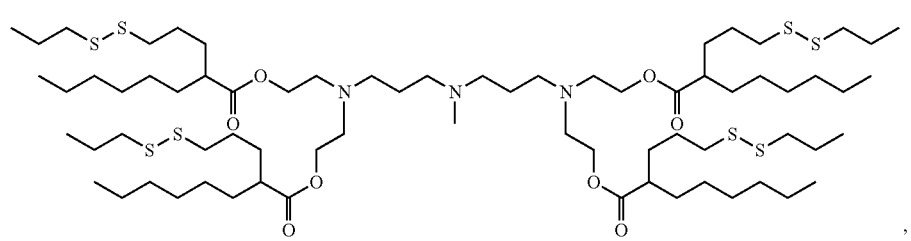
15
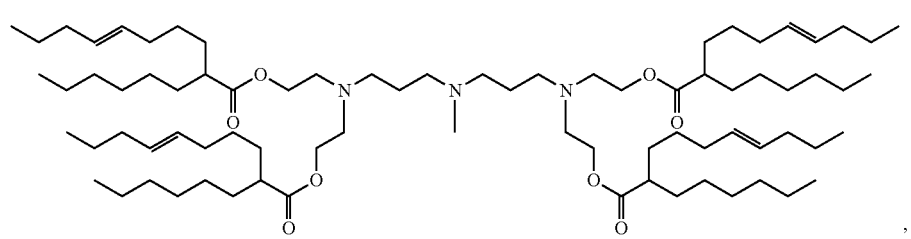
16

-continued
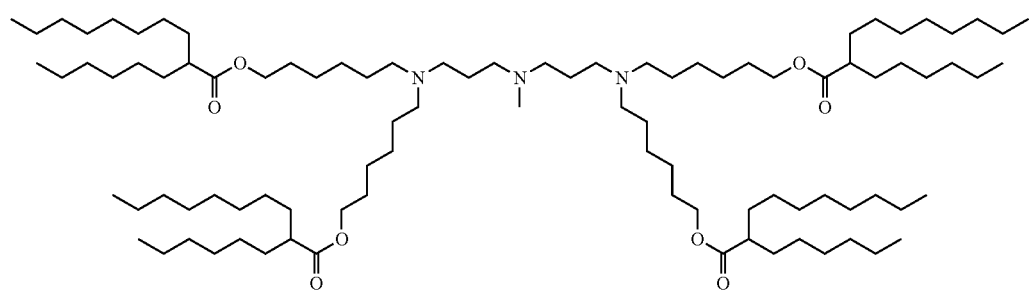
17
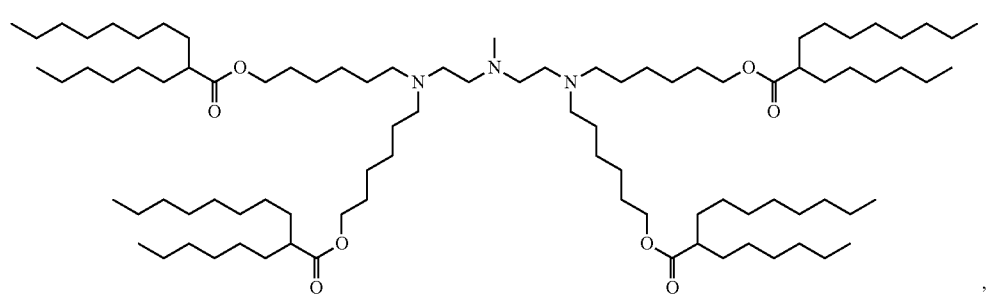
18
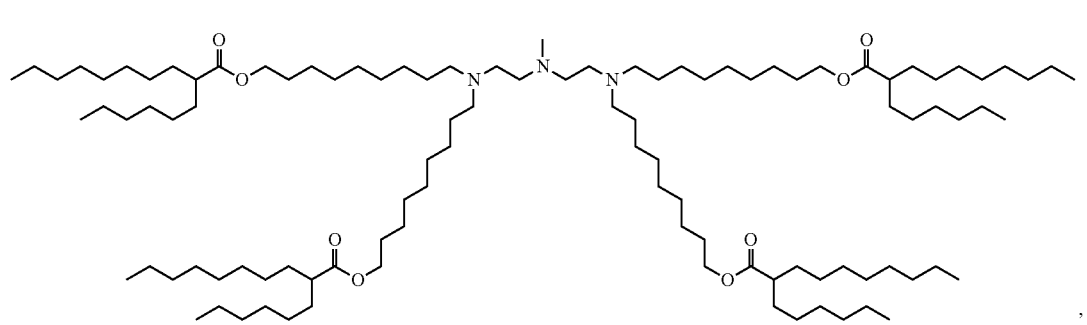
19
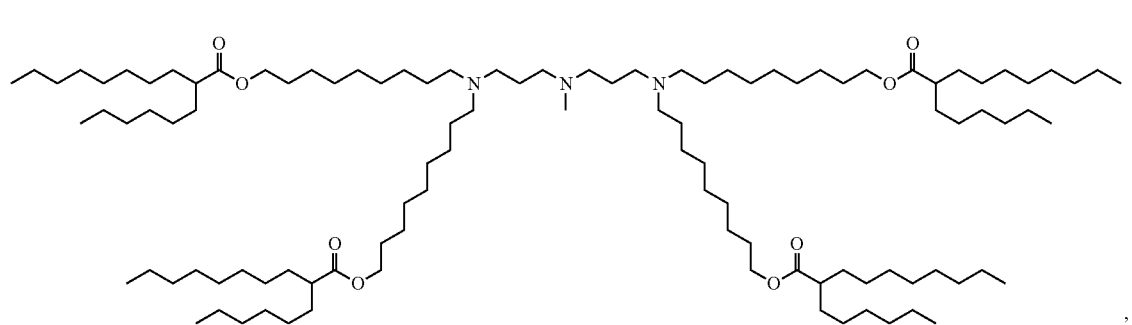
20
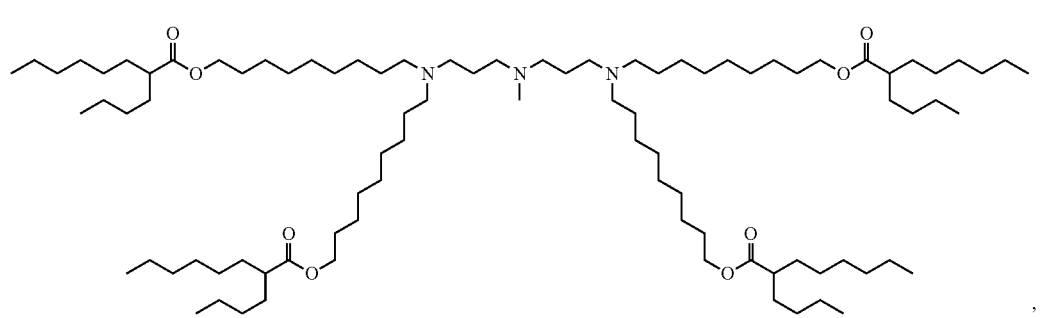
21

-continued
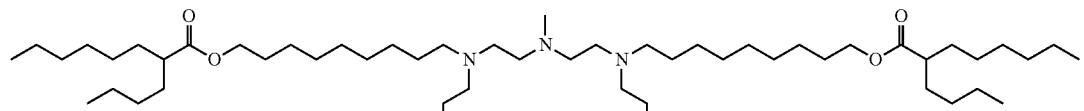
22
23
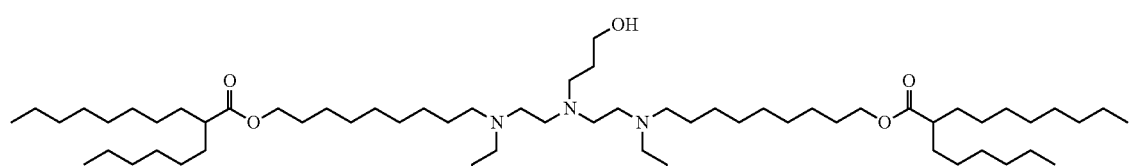
24
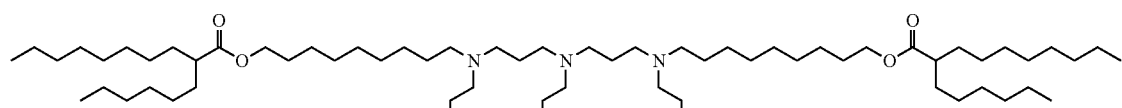
25
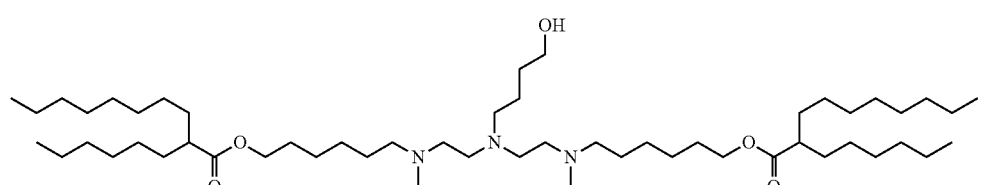
26
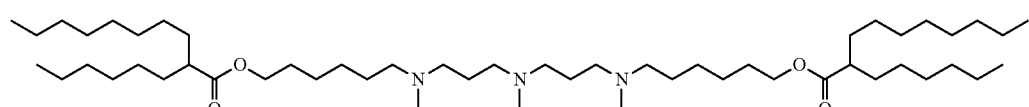
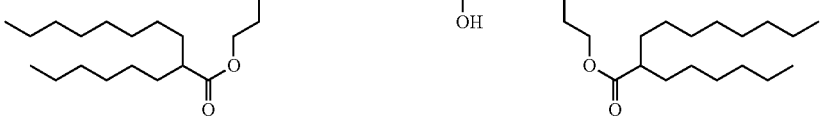

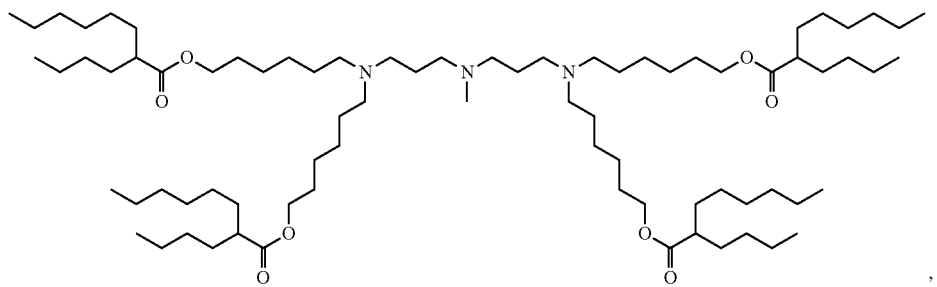
27
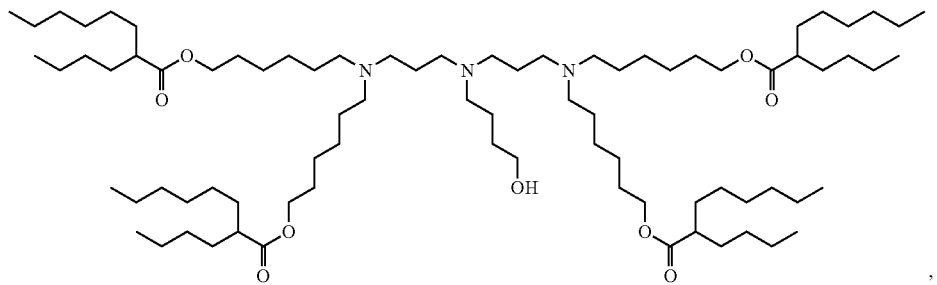
28
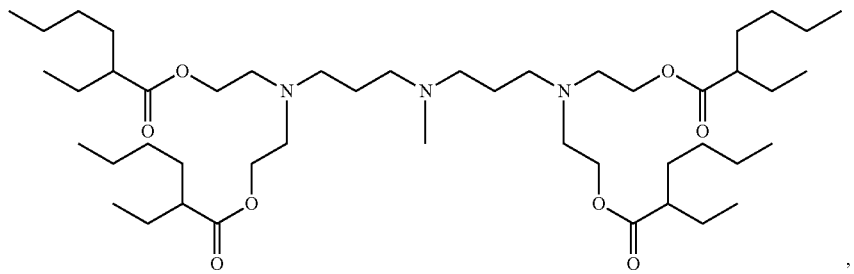
29
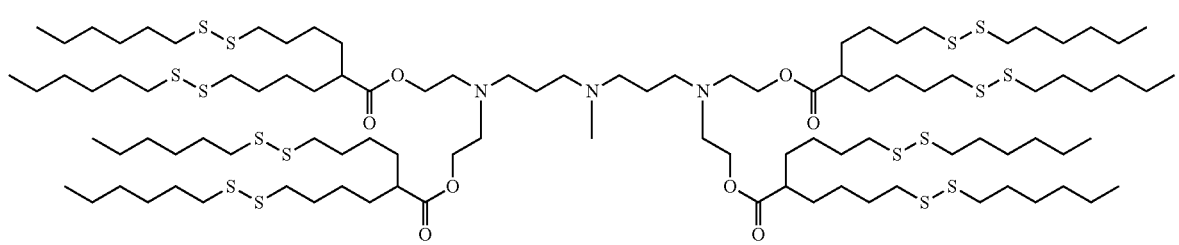
30
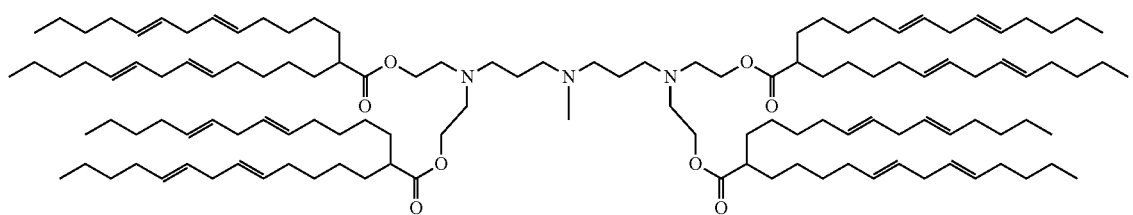
31
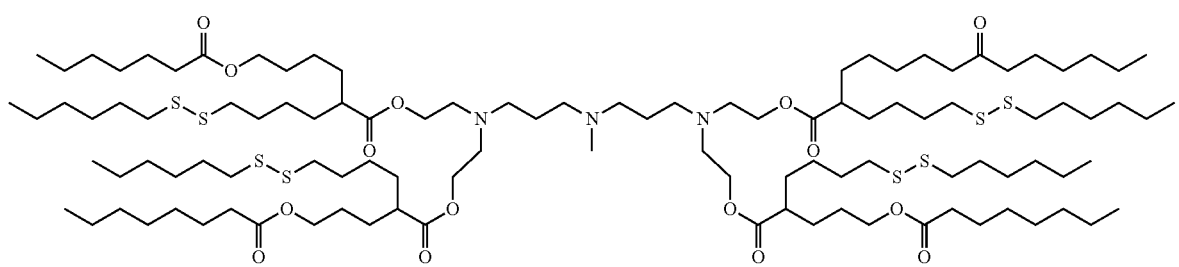
32

-continued
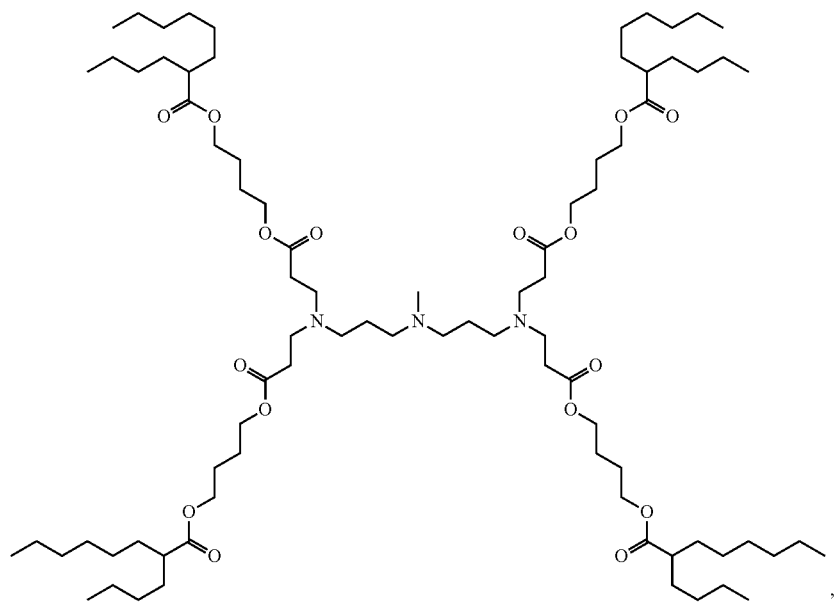
33
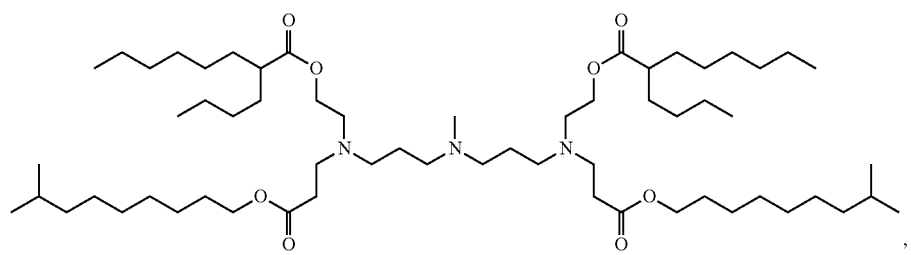
34
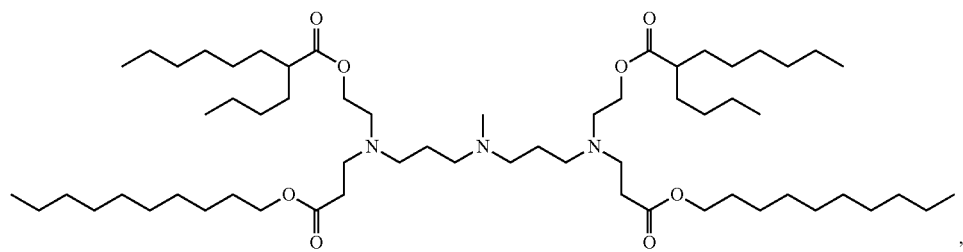
35
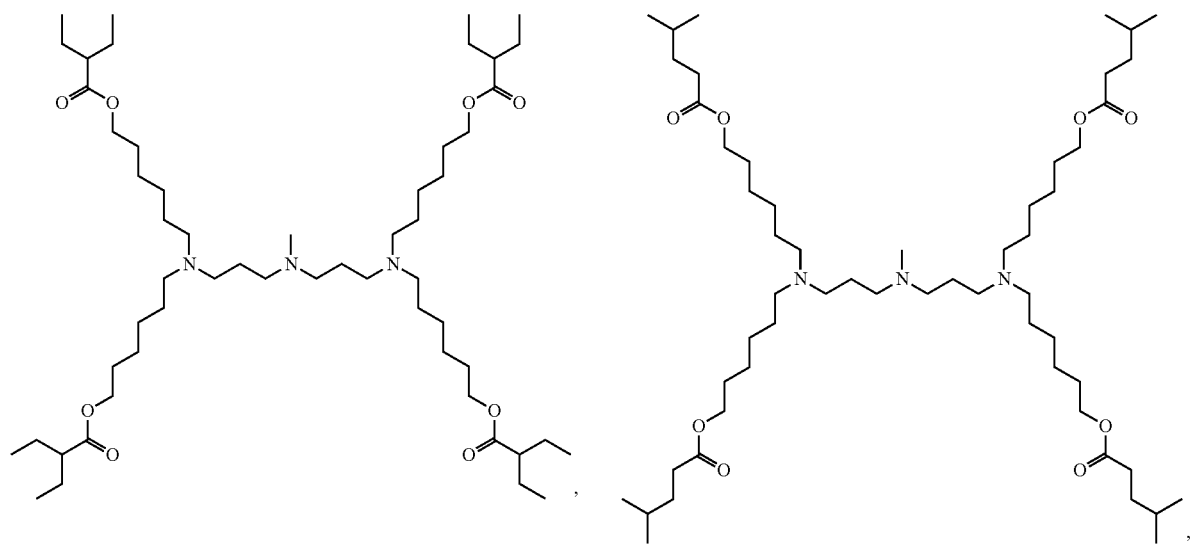
36 37

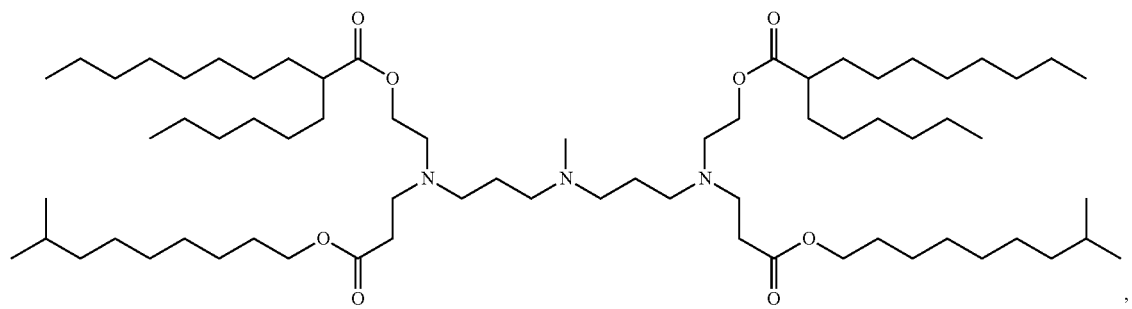
38
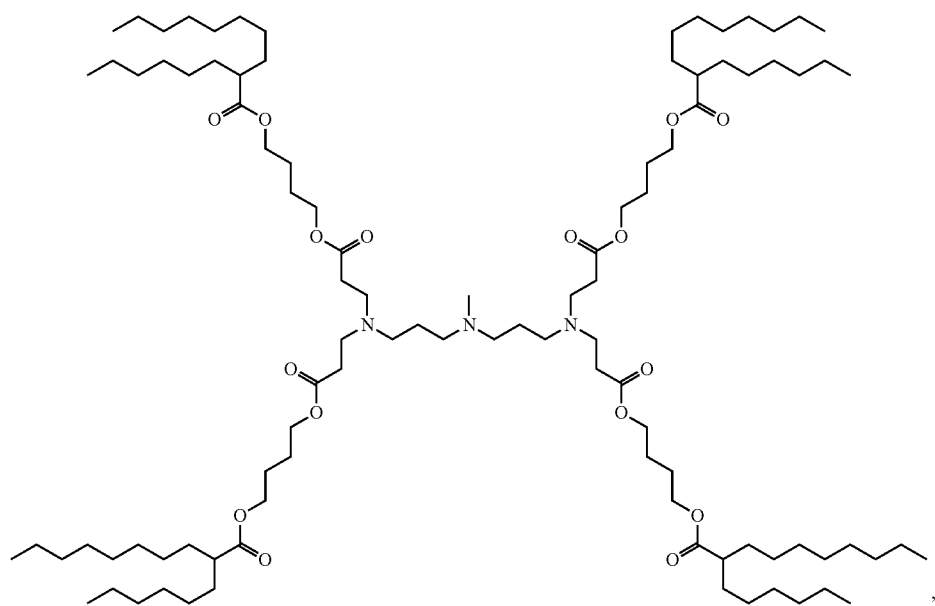
39
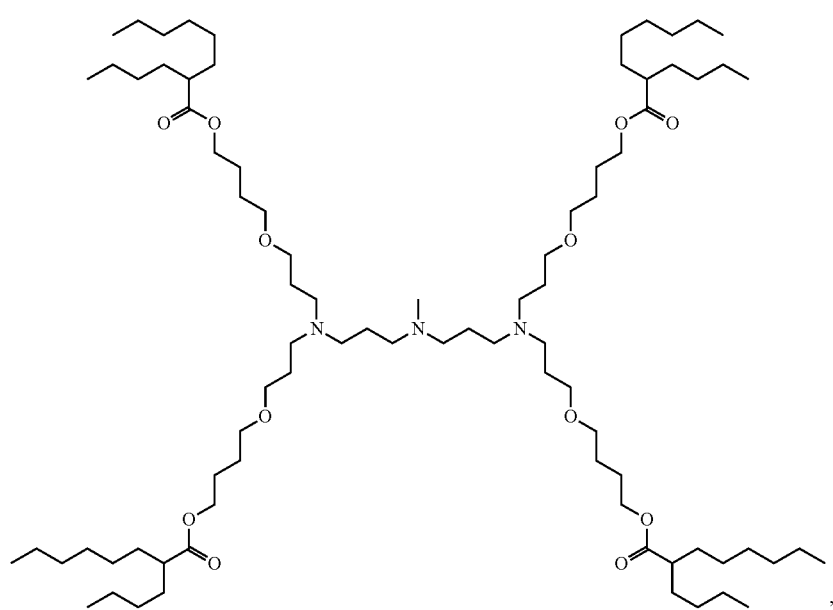
40

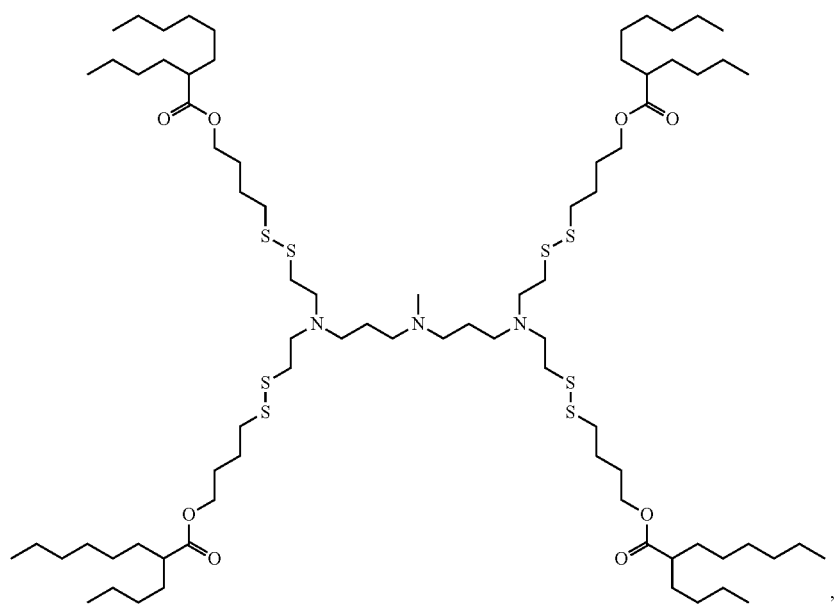
41
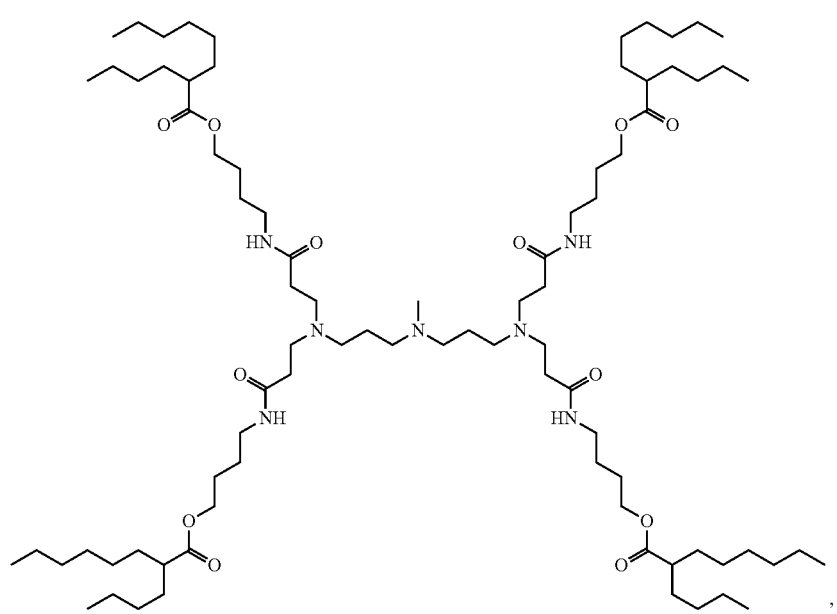
42

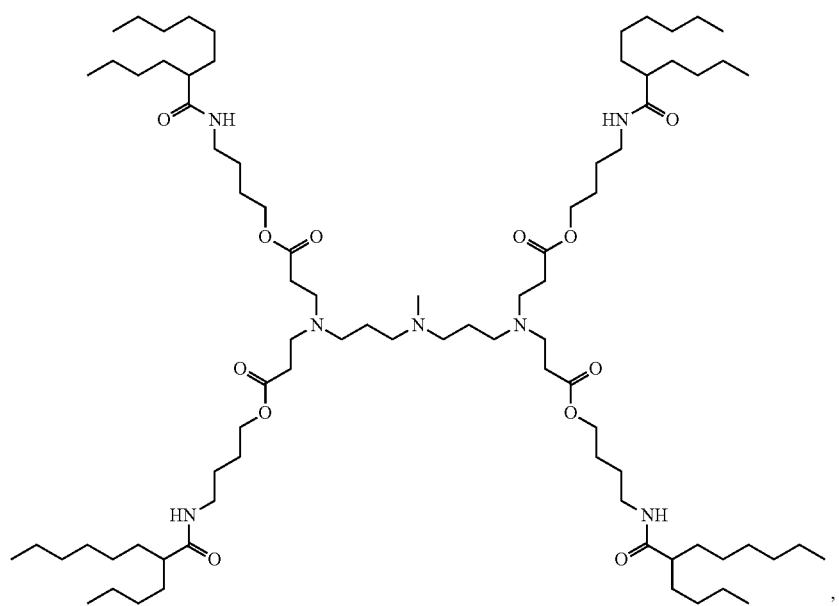
43
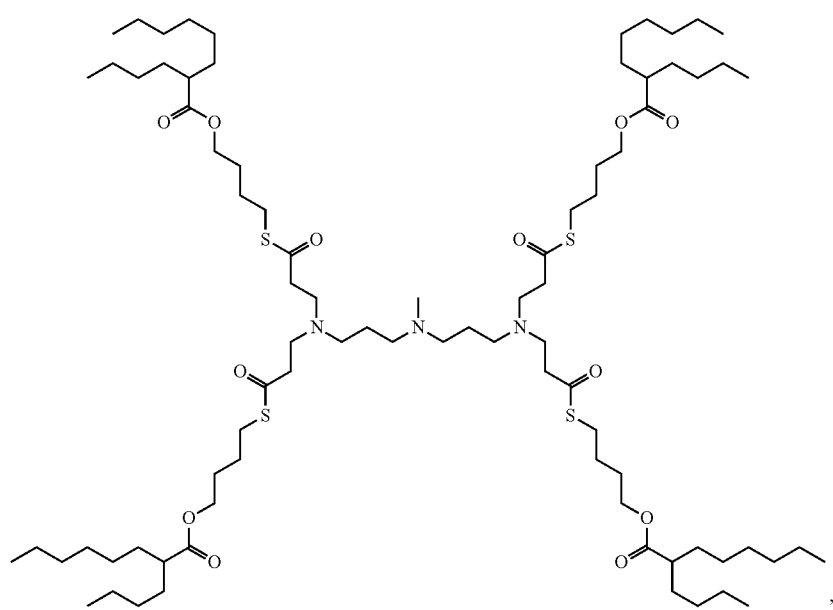
44

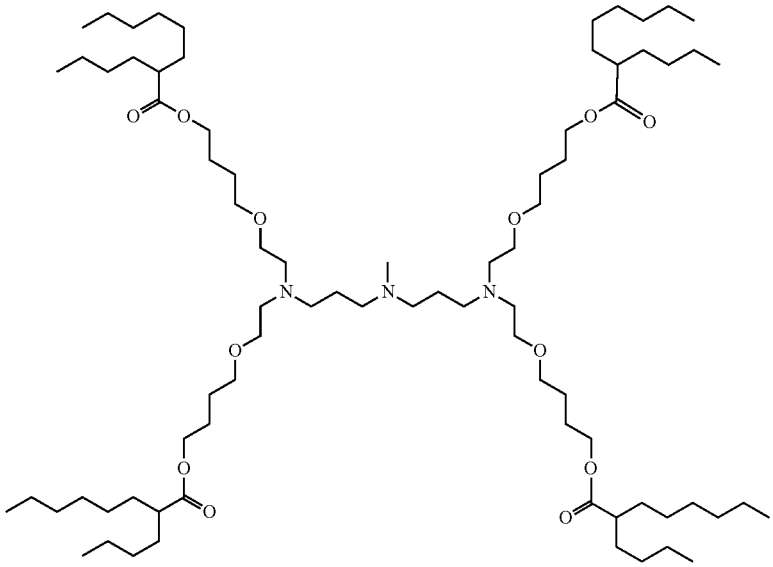

45

<Third Aspect>

The present disclosure provides a lipid vector, comprising the compound, or the pharmaceutically acceptable salt, the stereoisomer, the tautomer, the solvate, the chelate, the non-covalent complex or the prodrug thereof according to <First aspect> or <Second aspect>;

preferably, the lipid vector comprises a first lipid compound and a second lipid compound, wherein the first lipid compound comprises the compound, or the pharmaceutically acceptable salt, the stereoisomer, the tautomer, the solvate, the chelate, the non-covalent complex or the prodrug thereof according to <First aspect> or <Second aspect> and a cationic lipid, the second lipid compound comprises at least one selected from the group consisting of an anionic lipid, a neutral lipid, a sterol and an amphiphilic lipid;

preferably, the cationic lipid is at least one selected from the group consisting of DLinDMA, DODMA, DLin-MC2-MPZ, DLin-KC2-DMA, DOTAP, C12-200, DC-Chol and DOTMA;

the anionic lipid is at least one selected from the group consisting of phosphatidylserine, phosphatidylinositol, phosphatidic acid, phosphatidylglycerol, DOPG and dimyristoylphosphatidylglycerol;

the neutral lipid is at least one selected from the group consisting of DOPE, DSPC, DPPC, DOPC, DPPG, POPC, POPE, DPPE, DMPE, DSPE, SOPE, or a lipid obtained by modifying the above neutral lipid with an anionic or cationic modifying group;

the amphiphilic lipid is at least one selected from the group consisting of PEG-DMG, PEG-c-DMG, PEG-C14, PEG-c-DMA, PEG-DSPE, PEG-PE, a PEG-modified ceramide, a PEG-modified dialkylamine, a PEG-modified diacylglycerol, Tween-20, Tween-80, PEG-DPG, PEG-s-DMG, DAA, PEG-c-DOMG and GalNAc-PEG-DSG.

Further preferably, the molar ratio of the first lipid compound, the anionic lipid, the neutral lipid, the sterol and the amphiphilic lipid in the lipid vector is (20 to 65):(0 to 20):(5 to 25):(25 to 55):(0.3 to 15);

wherein in the first lipid compound, the molar ratio of the compound, or the pharmaceutically acceptable salt, the stereoisomer, the tautomer, the solvate, the chelate, the non-covalent complex or the prodrug thereof according to <First aspect> or <Second aspect> to the cationic lipid is (1 to 10):(0 to 10).

Further preferably, the molar ratio of the first lipid compound, the anionic lipid, the neutral lipid, the sterol and the amphiphilic lipid in the lipid vector is (20 to 55):(0 to 13):(5 to 25):(25 to 51.5):(0.5 to 10);

wherein in the first lipid compound, the molar ratio of the compound, or the pharmaceutically acceptable salt, the stereoisomer, the tautomer, the solvate, the chelate, the non-covalent complex or the prodrug thereof according to <First aspect> or <Second aspect> to the cationic lipid is (3 to 4):(0 to 5).

<Fourth Aspect>

The present disclosure provides a nucleic acid lipid nanoparticle composition, comprising the compound, or the pharmaceutically acceptable salt, the stereoisomer, the tautomer, the solvate, the chelate, the non-covalent complex or the prodrug thereof according to <First Aspect> or <Second aspect>, or the lipid vector according to <Third aspect>, and a nucleic acid drug;

preferably, the nucleic acid drug is at least one selected from the group consisting of a DNA, an siRNA, an mRNA, a dsRNA, an antisense nucleic acid, an microRNA, an antisense microRNA, antagomir, an microRNA inhibitor, an microRNA agonist and an immunostimulatory nucleic acid;

preferably, the mass ratio of the nucleic acid drug to the compound, or the pharmaceutically acceptable salt, the stereoisomer, the tautomer, the solvate, the chelate, the non-covalent complex or the prodrug thereof according to <First aspect> or <Second aspect> is 1:(3 to 40); or, the mass ratio of the nucleic acid drug to the lipid vector according to <Third aspect> is 1:(3 to 40).

Further preferably, the mass ratio of the nucleic acid drug to the compound, or the pharmaceutically acceptable salt, the stereoisomer, the tautomer, the solvate, the chelate, the non-covalent complex or the prodrug thereof according to <First aspect> or <Second aspect> is 1:(3 to 30), preferably 1:3 and 1:30; or, the mass ratio of the nucleic acid drug to the lipid vector according to <Third aspect> is 1:(3 to 30), preferably 1:3 and 1:30.

<Fifth Aspect>

The present disclosure provides a pharmaceutical preparation, comprising the compound, or the pharmaceutically acceptable salt, the stereoisomer, the tautomer, the solvate, the chelate, the non-covalent complex or the prodrug thereof according to <First aspect> or <Second aspect>, or the lipid vector according to <Third aspect>, or the nucleic acid lipid nanoparticle composition according to <Fourth aspect>, and a pharmaceutically acceptable excipient, carrier and diluent;

preferably, the pharmaceutical preparation has a particle size of 30 to 500 nm;

preferably, the encapsulation efficiency of the nucleic acid drug in the pharmaceutical preparation is higher than 50%.

Advantageous Effects of the Disclosure

The present disclosure provides a series of compounds of formula (I) with novel structures. This compound may be used as a cationic lipid and used in combination with other lipid compounds to prepare lipid vectors, which have controllable particle size, uniform distribution, monodispersity, and very high encapsulation efficiency for negatively charged drugs. In addition, the lipid vector is capable of exhibiting different potentials at different pH, exhibiting positive potential when encapsulating a negatively charged drug under acidic conditions such that the positively charged lipid vector and the negatively charged drug are attracted to each other; as well as exhibiting electrical neutrality in human body (i.e., a neutral condition) so as to avoid huge cytotoxicity. In addition, it is possible to select lipid compounds with different structures as lipid vectors to adjust the enrichment of nucleic acid drugs in different organs.

Further, this compound has a simple synthesis route with cheap and readily available raw materials, thereby showing very high market potential.

DETAILED DESCRIPTION

Figure 1:
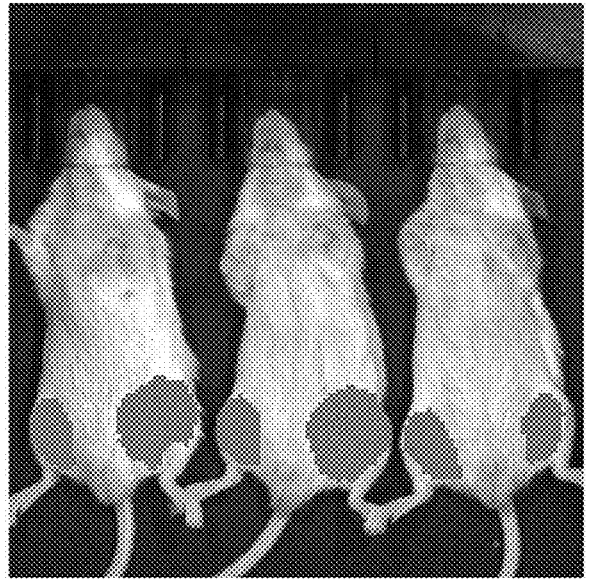
FIG. 1 shows the imaging results obtained 6 hours after the intramuscular injection of LNP@mRNA prepared by Compound 2 and other three lipids in Example 26.

Prior to further description of the present disclosure, it should be understood that the present disclosure is not limited to the specific embodiments described herein; and it should also be understood that the terms used herein are only used to describe rather than limit the specific embodiments.

Definition of Terms

Unless otherwise stated, the following terms have the meanings as below.

The term "pharmaceutically acceptable salt" refers to a salt of the compound of the present disclosure that is substantially non-toxic to living organisms. Pharmaceutically acceptable salts generally include, but are not limited to, salts formed by the reaction of the compound of the present disclosure with pharmaceutically acceptable inorganic/organic acids or inorganic/organic bases, and such salts are also referred to as acid addition salts or base addition salts. Common inorganic acids include, but are not limited to, hydrochloric acid, hydrobromic acid, sulfuric acid, phosphoric acid, and the like. Common organic acids include, but are not limited to, trifluoroacetic acid, citric acid, maleic acid, fumaric acid, succinic acid, tartaric acid, lactic acid, pyruvic acid, oxalic acid, formic acid, acetic acid, benzoic acid, methanesulfonic acid, benzenesulfonic acid, p-toluenesulfonic acid, and the like. Common inorganic bases include, but are not limited to, sodium hydroxide, potassium hydroxide, calcium hydroxide, barium hydroxide, and the like. Common organic bases include, but are not limited to, diethylamine, triethylamine, ethambutol, and the like.

The term "stereoisomer" (also called "optical isomer") refers to a stable isomer that has a vertical asymmetric plane resulted from at least one chiral factor (including chiral center, chiral axis, chiral plane, etc.), thus being capable of rotating the plane polarized light. Since there are asymmetric centers and other chemical structures that may cause stereoisomerism in the compound of the present disclosure, the present disclosure also includes these stereoisomers and mixtures thereof. Since the compound of the present disclosure and the salts thereof comprise asymmetric carbon atom(s), it is possible to exist in the form of a single stereoisomer as well as the form of a mixture of racemates, enantiomers and diastereomers. Generally, these compounds may be prepared in the form of racemic mixtures. However, if necessary, such compound may be prepared and isolated to obtain a pure stereoisomer, that is, a single enantiomer or diastereomer, or, a mixture of enriched single stereoisomer (purity ≥98%, ≥95%, ≥93%, ≥90%, ≥88%, ≥85%, or ≥80%). A single stereoisomer of the compound is synthetically prepared from an optically active starting material comprising the required chiral center, or obtained by preparing a mixture of enantiomeric products followed by separation or resolution (for example, converting the mixture of enantiomeric products to a mixture of diastereomers followed by separation or recrystallization, chromatographic process, or the use of chiral resolution reagents), or obtained by directly separating the enantiomers on a chiral chromatographic column. Starting compounds with specific stereochemistry are not only commercially available, but also may be prepared in accordance with the methods described below and then resolved by methods well known in the art.

The term "tautomers" (also called "tautomeric forms") refers to structural isomers with different energies that are capable of being converted into each other via low energy barrier. If tautomerism is possible (such as in a solution), it may reach the chemical equilibrium of tautomers. For example, proton tautomers (also called proton-transferred tautomers) include, but are not limited to, interconversion via proton migration, such as keto-enol isomerization, imine-enamine isomerization, amide-iminol isomerization, and the like. Unless otherwise indicated, all tautomeric forms of the compounds of the present disclosure fall within the scope of the present disclosure.

The term "solvate" refers to a substance formed by the binding of the compound of the present disclosure or a pharmaceutically acceptable salt thereof with at least one solvent molecule via non-covalent intermolecular forces. Common solvates include, but are not limited to, hydrates, ethanolates, acetonates, and the like.

The term "chelate" means a complex having a cyclic structure, which is obtained by the chelation by which a chelating ring is formed among two or more ligands and a same metal ion.

The term "non-covalent complex" means a complex formed by the interaction between a compound and another molecule, wherein no covalent bond is formed between the compound and the molecule. For example, complexation occurs via van der Waals interaction, bonding of hydrogen bond and electrostatic interaction (also referred to as ionic bonding).

The term "prodrug" refers to a derivative compound capable of directly or indirectly providing the compound of the present disclosure after administered to a patient. Particularly preferred derivative compounds or prodrugs are compounds capable of increasing the bioavailability of the compound of the present disclosure when being administered to a patient (for example, easier absorption into blood), or compounds capable of promoting the delivery of parent compounds to the sites of action (for example, lymphatic system). Unless otherwise indicated, all prodrug forms of the compounds of the present disclosure fall within the scope of the present disclosure, and various prodrug forms are well known in the art.

The term "each independently" means that at least two groups (or ring systems) having same or similar value ranges and existing in the same structure may have same or different meanings in a specific situation. For example, if substituent X and substituent Y is each independently hydrogen, halogen, hydroxy, cyano, alkyl, or aryl, when substituent X is hydrogen, substituent Y may be hydrogen, and may also be halogen, hydroxy, cyano, alkyl, or aryl; similarly, when substituent Y is hydrogen, substituent X may be hydrogen, and may also be halogen, hydroxy, cyano, alkyl, or aryl.

The term "optional" or "optionally" means that the event or situation described later may or may not occur, and this description includes the case where the event or situation occurs and the case where the event or situation does not occur.

Unless otherwise specified, all experimental methods described in the following Examples are conventional methods. Unless otherwise specified, all reagents and materials described in the following Examples are commercially available.

In the present disclosure, "equivalent (eq)" ratio refers to the molar ratio of the solvents or the reagents.

In the present disclosure, "an appropriate amount" means that the amount of the added solvent or reagent may be adjusted in a relatively large range and has little effect on synthesis, and said amount may not need specific limitation.

In the following Examples, the solvents and reagents used are all analytical pure or chemically pure, all solvents are subjected to redistillation prior to use, and all anhydrous solvents are processed in accordance with standard methods or methods recited in literatures.

EXAMPLES

Example 1 Synthesis of Compound 1

2-Hexyldecanoic acid (1.5 eq) was dissolved in an appropriate amount of dichloromethane, and DMAP (0.5 eq) and EDC (1.5 eq) were added to activate the carboxyl group. After 30 min, 2-bromoethanol (1.0 eq) was added thereto, and the resulting mixture was stirred at room temperature for 16 h. It was confirmed by TLC that the reaction of 2-bromoethanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, N,N-bis(3-aminopropyl) methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 1. $^1$H NMR (400 MHz, CDCl$_3$) δ 4.42-4.26 (d, 8H), 3.34-3.01 (d, 8H), 2.56-2.49 (d, 8H), 2.46-2.36 (m, 4H), 2.26 (s, 3H), 1.75-1.14 (m, 100H), 0.88-0.79 (m, 24H).

Example 2 Synthesis of Compound 2

2-Butyloctanoic acid (1.5 eq) was dissolved in an appropriate amount of dichloromethane, and DMAP (0.5 eq) and EDC (1.5 eq) were added to activate the carboxyl group. After 30 min, 2-bromoethanol (1.0 eq) was added thereto, and the resulting mixture was stirred at room temperature for 16 h. It was confirmed by TLC that the reaction of 2-bromoethanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, N,N-bis(3-aminopropyl) methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 2. $^1$H NMR (400 MHz, CDCl$_3$) δ 4.45-4.21 (d, 8H), 3.41-3.11 (d, 8H), 2.64-2.52 (d, 8H), 2.50-2.41 (m, 4H), 2.19 (s, 3H), 1.77-1.11 (m, 68H), 0.90-0.80 (m, 24H).

Example 3 Synthesis of Compound 3

2-Hexyldecanoic acid (1.5 eq) was dissolved in an appropriate amount of dichloromethane, and DMAP (0.5 eq) and EDC (1.5 eq) were added to activate the carboxyl group.

After 30 min, 3-bromopropanol (1.0 eq) was added thereto, and the resulting mixture was stirred at room temperature for 16 h. It was confirmed by TLC that the reaction of 3-bromopropanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, N,N-bis(3-aminopropyl)methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 3. $^1$H NMR (400 MHz, CDCl$_3$) δ 4.27-4.24 (d, 8H), 2.63-2.59 (d, 8H), 2.56-2.49 (d, 8H), 2.39-2.31 (m, 4H), 2.19 (s, 3H), 1.69-1.24 (m, 108H), 0.93-0.81 (m, 24H).

Example 4 Synthesis of Compound 4

2-Hexyldecanoic acid (1.5 eq) was dissolved in an appropriate amount of dichloromethane, and DMAP (0.5 eq) and EDC (1.5 eq) were added to activate the carboxyl group. After 30 min, 3-bromopropanol (1.0 eq) was added thereto, and the resulting mixture was stirred at room temperature for 16 h. It was confirmed by TLC that the reaction of 3-bromopropanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, 3-(bis(3-aminopropyl)amino)-1-propanol (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of 3-(bis(3-aminopropyl)amino)-1-propanol was complete. The resultant was subjected to column chromatography with a mobile phase consisting of methanol and dichloromethane and then concentrated, so as to afford Compound 4. $^1$H NMR (400 MHz, CDCl$_3$) δ 4.16-4.10 (d, 8H), 3.52-3.49 (d, 2H), 2.49-2.46 (d, 10H), 2.38-2.35 (d, 8H), 2.15-2.10 (m, 4H), 1.74-1.31 (m, 110H), 0.95-0.89 (m, 24H).

Example 5 Synthesis of Compound 7

2-Octylundecanoic acid (1.5 eq) was dissolved in an appropriate amount of dichloromethane, and DMAP (0.5 eq) and EDC (1.5 eq) were added to activate the carboxyl group. After 30 min, 2-bromoethanol (1.0 eq) was added thereto, and the resulting mixture was stirred at room temperature for 16 h. It was confirmed by TLC that the reaction of 2-bromoethanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, N,N-bis(3-aminopropyl)methylamine (1.0 eq) was dissolved in an appropriate amount of ethanol, potassium carbonate (4.8 eq) was added thereto, and the resulting mixture was stirred and reacted to at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 7. $^1$H NMR (400 MHz, CDCl$_3$) δ 4.38-4.20 (d, 8H), 3.24-3.06 (d, 8H), 2.53-2.42 (d, 8H), 2.45-2.34 (m, 4H), 2.22 (s, 3H), 1.81-1.11 (m, 124H), 0.89-0.78 (m, 24H).

Example 6 Synthesis of Compound 9

2-(2-(Butyldisulfanyl)ethyl)octanoic acid (1.5 eq) was dissolved in an appropriate amount of dichloromethane, and DMAP (0.5 eq) and EDC (1.5 eq) were added to activate the carboxyl group. After 30 min, 2-bromoethanol (1.0 eq) was added thereto, and the resulting mixture was stirred at room temperature for 16 h. It was confirmed by TLC that the reaction of 2-bromoethanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, N,N-bis(3-aminopropyl)methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 9. $^1$H NMR (400 MHz, CDCl$_3$) δ 4.35-4.30 (d, 8H), 2.98-2.89 (d, 8H), 2.65-2.59 (m, 16H), 2.46-2.36 (m, 8H), 2.30-2.19 (m, 4H), 2.10 (s, 3H), 1.92-1.14 (m, 68H), 0.93-0.87 (m, 24H).

Example 7 Synthesis of Compound 11

2-Hexyldecanoic acid (1.5 eq) was dissolved in an appropriate amount of dichloromethane, and DMAP (0.5 eq) and EDC (1.5 eq) were added to activate the carboxyl group. After 30 min, 2-bromoethanol (1.0 eq) was added thereto, and the resulting mixture was stirred at room temperature for 16 h. It was confirmed by TLC that the reaction of 2-bromoethanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, 4-(bis(3-aminopropyl)amino)-1-butanol (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of 4-(bis(3-aminopropyl)amino)-1-butanol was complete. The resultant was subjected to column chromatography with a mobile phase consisting of methanol and dichloromethane and then concentrated, so as to afford Compound 11. $^1$H NMR (400 MHz, CDCl$_3$) δ 4.28-4.20 (d, 8H), 3.51-3.42 (d, 2H), 3.08-2.91 (m, 10H), 2.48-2.40 (m, 8H), 2.15-2.08 (m, 4H), 1.65-1.14 (m, 104H), 0.92-0.87 (m, 24H).

Example 8 Synthesis of Compound 12

2-Butyloctanoic acid (1.5 eq) was dissolved in an appropriate amount of dichloromethane, and DMAP (0.5 eq) and EDC (1.5 eq) were added to activate the carboxyl group. After 30 min, 2-bromoethanol (1.0 eq) was added thereto, and the resulting mixture was stirred at room temperature for 16 h. It was confirmed by TLC that the reaction of 2-bromoethanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, 4-(bis(3-aminopropyl)amino)-1-butanol (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of 4-(bis(3-aminopropyl)amino)-1-butanol was complete. The resultant was subjected to column chromatography with a mobile phase consisting of methanol and dichloromethane and then concentrated, so as to afford Compound 12. $^1$H NMR (400 MHz, CDCl$_3$) δ 4.34-4.25 (d, 8H), 3.50-3.43 (d, 2H), 3.15-2.98 (m, 10H), 2.45-2.38 (m, 8H), 2.14-2.05 (m, 4H), 1.68-1.15 (m, 72H), 0.90-0.85 (m, 24H).

Example 9 Synthesis of Compound 15

2-(3-(Propyldisulfanyl)propyl)octanoic acid (1.5 eq) was dissolved in an appropriate amount of dichloromethane, and DMAP (0.5 eq) and EDC (1.5 eq) were added to activate the carboxyl group. After 30 min, 2-bromoethanol (1.0 eq) was added thereto, and the resulting mixture was stirred at room temperature for 16 h. It was confirmed by TLC that the reaction of 2-bromoethanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, N,N-bis(3-aminopropyl)methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 15. $^1$H NMR (400 MHz, CDCl$_3$) δ 4.25-4.17 (d, 8H), 3.05-2.96 (d, 8H), 2.62-2.54 (m, 16H), 2.46-2.41 (m, 8H), 2.31-2.26 (m, 4H), 2.14 (s, 3H), 1.64-1.16 (m, 68H), 1.01-0.86 (m, 24H).

Example 10 Synthesis of Compound 17

2-Hexyldecanoic acid (1.5 eq) was dissolved in an appropriate amount of dichloromethane, and DMAP (0.5 eq) and EDC (1.5 eq) were added to activate the carboxyl group. After 30 min, 6-bromohexanol (1.0 eq) was added thereto, and the mixture was stirred at room temperature overnight. It was confirmed by TLC that the reaction of 6-bromohexanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, 2 mL of N,N-bis(3-aminopropyl)methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 17. $^1$H NMR (400 MHz, CDCl$_3$) δ 4.11-4.07 (d, 8H), 3.33-3.20 (d, 8H), 2.75-2.62 (d, 8H), 2.55-2.51 (m, 4H), 2.23 (s, 3H), 1.92-1.07 (m, 132H), 0.95-0.88 (m, 24H).

Example 11 Synthesis of Compound 20

2-Hexyldecanoic acid (1.5 eq) was dissolved in an appropriate amount of dichloromethane, and DMAP (0.5 eq) and EDC (1.5 eq) were added to activate the carboxyl group. After 30 min, 9-bromo-1-nonanol (1.0 eq) was added thereto, and the resulting mixture was stirred at room temperature for 16 h. It was confirmed by TLC that the reaction of 9-bromo-1-nonanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, N,N-bis(3-aminopropyl)methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 20. $^1$H NMR (400 MHz, CDCl$_3$) δ 4.11-4.05 (d, 8H), 3.05-2.97 (d, 8H), 2.56-2.49 (d, 8H), 2.41-2.32 (m, 4H), 2.26 (s, 3H), 1.79-1.13 (m, 156H), 0.90-0.79 (m, 24H).

Example 12 Synthesis of Compound 21

2-Butyloctanoic acid (1.5 eq) was dissolved in an appropriate amount of dichloromethane, and DMAP (0.5 eq) and EDC (1.5 eq) were added to activate the carboxyl group. After 30 min, 9-bromo-1-nonanol (1.0 eq) was added thereto, and the resulting mixture was stirred at room temperature for 16 h. It was confirmed by TLC that the reaction of 9-bromo-1-nonanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, N,N-bis(3-aminopropyl)methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 21. $^1$H NMR (400 MHz, CDCl$_3$) δ 4.13-4.06 (d, 8H), 3.08-2.93 (d, 8H), 2.52-2.45 (d, 8H), 2.40-2.31 (m, 4H), 2.25 (s, 3H), 1.78-1.11 (m, 124H), 0.93-0.78 (m, 24H).

Example 13 Synthesis of Compound 24

2-Hexyldecanoic acid (1.5 eq) was dissolved in an appropriate amount of dichloromethane, and DMAP (0.5 eq) and EDC (1.5 eq) were added to activate the carboxyl group. After 30 min, 9-bromo-1-nonanol (1.0 eq) was added thereto, and the resulting mixture was stirred at room temperature for 16 h. It was confirmed by TLC that the reaction of 9-bromo-1-nonanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, 3-(bis(3-aminopropyl) amino)-1-propanol (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of 3-(bis(3-aminopropyl)amino)-1-propanol was complete. The resultant was subjected to column chromatography with a mobile phase consisting of methanol and dichloromethane and then concentrated, so as to afford Compound 24. $^1$H NMR (400 MHz, CDCl$_3$) δ 4.08-4.06 (d, 8H), 3.52-3.48 (d, 2H), 3.11-3.02 (d, 8H), 2.54-2.45 (d, 10H), 2.21-2.18 (m, 4H), 1.75-1.21 (m, 158H), 0.88-0.80 (m, 24H).

Example 14 Synthesis of Compound 26

2-Hexyldecanoic acid (1.5 eq) was dissolved in an appropriate amount of dichloromethane, and DMAP (0.5 eq) and EDC (1.5 eq) were added to activate the carboxyl group. After 30 min, 6-bromohexanol (1.0 eq) was added thereto, and the resulting mixture was stirred at room temperature for 16 h. It was confirmed by TLC that the reaction of 6-bromohexanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, 4-(bis(3-aminopropyl) amino)-1-butanol (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of 4-(bis(3-aminopropyl)amino)-1-butanol was complete. The resultant was subjected to column chromatography with a mobile phase consisting of methanol and dichloromethane and then concentrated, so as to afford Compound 26. $^1$H NMR (400 MHz, CDCl$_3$) δ 4.11-4.08 (d, 8H), 3.51-3.47 (d, 2H), 3.08-3.01 (d, 10H), 2.51-2.42 (d, 8H), 2.23-2.15 (m, 4H), 1.71-1.16 (m, 136H), 0.92-0.83 (m, 24H).

Example 15 Synthesis of Compound 27

2-Butyloctanoic acid (1.5 eq) was dissolved in an appropriate amount of dichloromethane, and DMAP (0.5 eq) and EDC (1.5 eq) were added to activate the carboxyl group. After 30 min, 6-bromohexanol (1.0 eq) was added thereto, and the mixture was stirred at room temperature overnight. It was confirmed by TLC that the reaction of 6-bromohexanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, 2 mL of N,N-bis(3-aminopropyl)methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 27. $^1$H NMR (400 MHz, CDCl$_3$) δ 4.15-4.02 (d, 8H), 3.23-3.21 (d, 8H), 2.65-2.60 (d, 8H), 2.49-2.38 (m, 4H), 2.11 (s, 3H), 1.86-1.12 (m, 100H), 0.92-0.85 (m, 24H).

Example 16 Synthesis of Compound 28

2-Butyloctanoic acid (1.5 eq) was dissolved in an appropriate amount of dichloromethane, and DMAP (0.5 eq) and EDC (1.5 eq) were added to activate the carboxyl group. After 30 min, 6-bromohexanol (1.0 eq) was added thereto, and the resulting mixture was stirred at room temperature for 16 h. It was confirmed by TLC that the reaction of 6-bromohexanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, 4-(bis(3-aminopropyl) amino)-1-butanol (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of 4-(bis(3-aminopropyl)amino)-1-butanol was complete. The resultant was subjected to column chromatography with a mobile phase consisting of methanol and dichloromethane and then concentrated, so as to afford Compound 28. $^1$H NMR (400 MHz, CDCl$_3$) δ 4.13-4.07 (d, 8H), 3.50-3.46 (d, 2H), 3.09-3.02 (d, 10H), 2.50-2.43 (d, 8H), 2.24-2.15 (m, 4H), 1.68-1.18 (m, 104H), 0.93-0.85 (m, 24H).

Example 17 Synthesis of Compound 29

2-Ethylhexanoic acid (1.5 eq) was dissolved in an appropriate amount of dichloromethane, and DMAP (0.5 eq) and EDC (1.5 eq) were added to activate the carboxyl group. After 30 min, 2-bromoethanol (1.0 eq) was added thereto, and the resulting mixture was stirred at room temperature for 16 h. It was confirmed by TLC that the reaction of 2-bromoethanol was complete. The resultant was extracted with saturated sodium bicarbonate solution for several times, dried over anhydrous sodium sulfate, filtered and concentrated, so as to afford a brominated intermediate.

The brominated intermediate (4.8 eq) was added to an appropriate amount of ethanol, N,N-bis(3-aminopropyl) methylamine (1.0 eq) was dissolved in an appropriate amount of ethanol, potassium carbonate (4.8 eq) was added thereto, and the resulting mixture was stirred and reacted at 110° C. under reflux overnight. It was confirmed by TLC that the reaction of N,N-bis(3-aminopropyl)methylamine was complete. The resultant was subjected to column chromatography with a mobile phase consisting of methanol and dichloromethane and then concentrated, so as to afford Compound 29. $^1$H NMR (400 MHz, CDCl$_3$) δ 4.22-4.18 (d, 8H), 3.11-2.98 (d, 8H), 2.46-2.38 (d, 8H), 2.30-2.21 (m, 4H), 2.16 (s, 3H), 1.86-1.32 (m, 36H), 0.95-0.86 (m, 24H).

Example 18 Synthesis of Compound 33

2-Butyloctanoic acid (1.5 eq) was dissolved in an appropriate amount of dichloromethane and stirred. EDC (1.5 eq), DMAP (0.5 eq) and triethylamine (1 eq) were added thereto, and the mixture was stirred at room temperature for 0.5 h. 4-Hydroxybutyl acrylate (1.0 eq) was added thereto, and the mixture was reacted at room temperature overnight. It was confirmed by TLC that the reaction of the raw materials was complete. Acetic acid was added to adjust pH to 6 to 7, and the resultant was extracted several times and then subjected to column chromatography, so as to afford a colorless and transparent liquid.

The above-mentioned resulting colorless and transparent liquid (4.8 eq) was dissolved in an appropriate amount of methanol, potassium carbonate (4.8 eq) was added thereto, N,N-bis(3-aminopropyl)methylamine (1.0 eq) was then added thereto, and the mixture was stirred at 75° C. overnight. The completion of the reaction of the raw materials was monitored by TLC, and the reaction solution was concentrated. The resultant was subjected to column chromatography with a mobile phase consisting of methanol and dichloromethane and then concentrated, so as to afford Compound 33. $^1$H NMR (400 MHz, CDCl$_3$) δ 4.11-4.05 (d, 16H), 2.76-2.72 (d, 8H), 2.43-2.39 (d, 12H), 2.32-2.25 (m, 8H), 2.16 (s, 3H), 1.71-1.17 (m, 84H), 0.87-0.83 (m, 24H).

Example 19 Synthesis of Compound 34

2-Butyloctanoic acid (1.5 eq) was dissolved in an appropriate amount of dichloromethane and stirred. EDC (1.5 eq), DMAP (0.5 eq) and triethylamine (1.0 eq) were added thereto, and the mixture was stirred at room temperature for 0.5 h. 2-Bromoethanol (1.0 eq) was added thereto, and the mixture was reacted at room temperature overnight. It was confirmed by TLC that the reaction of the raw materials was complete. Acetic acid was added to adjust pH to 6 to 7. The resultant was extracted several times, subjected to column chromatography with a mobile phase consisting of methanol and dichloromethane, and then concentrated, so as to afford a colorless and transparent liquid.

The above-mentioned resulting colorless and transparent liquid (2.1 eq) was dissolved in an appropriate amount of ethanol, potassium carbonate (2.4 eq) was added, N,N-bis(3-aminopropyl)methylamine (1.0 eq) was then added thereto, and the mixture was stirred at 75° C. overnight. The completion of the reaction of the raw materials was monitored by TLC, and the reaction solution was concentrated. The resultant was subjected to column chromatography with a mobile phase consisting of methanol and dichloromethane and concentrated, so as to afford a pale yellow oil.

The above-mentioned resulting oil (1.0 eq) was dissolved in an appropriate amount of methanol, isodecyl acrylate (2.5 eq) was added, and the mixture was stirred at 45° C. overnight. The completion of the reaction of the raw materials was monitored by TLC, and the reaction solution was concentrated. The resultant was subjected to column chromatography with a mobile phase consisting of methanol and dichloromethane and then concentrated, so as to afford Compound 34. $^1$H NMR (400 MHz, CDCl$_3$) δ 4.23-4.19 (m, 8H), 3.74-3.70 (d, 4H), 2.87-2.84 (d, 4H), 2.52-2.41 (m, 12H), 2.31-2.25 (m, 2H), 2.08 (s, 3H), 1.76-1.14 (m, 62H), 0.91-0.83 (m, 24H).

Example 20 Synthesis of Compound 35

2-Butyloctanoic acid (1.5 eq) was dissolved in an appropriate amount of dichloromethane and stirred. EDC (1.5 eq), DMAP (0.5 eq) and triethylamine (1.0 eq) were added thereto, and the mixture was stirred at room temperature for 0.5 h. 2-Bromoethanol (1.0 eq) was added thereto, and the mixture was reacted at room temperature overnight. It was confirmed by TLC that the reaction of the raw materials was complete. Acetic acid was added to adjust pH to 6 to 7. The resultant was extracted several times, subjected to column chromatography with a mobile phase consisting of methanol and dichloromethane, and then concentrated, so as to afford a colorless and transparent liquid.

The above-mentioned resulting colorless and transparent liquid (2.1 eq) was dissolved in an appropriate amount of ethanol, potassium carbonate (2.4 eq) was added, N,N-bis(3-aminopropyl)methylamine (1.0 eq) was then added thereto, and the mixture was stirred at 75° C. overnight. The completion of the reaction of the raw materials was monitored by TLC, and the reaction solution was concentrated. The resultant was subjected to column chromatography with a mobile phase consisting of methanol and dichloromethane and concentrated, so as to afford a pale yellow oil.

The above-mentioned resulting oil (1.0 eq) was dissolved in an appropriate amount of methanol, decyl acrylate (2.5 eq) was added, and the mixture was stirred at 45° C. overnight. The completion of the reaction of the raw materials was monitored by TLC, and the reaction solution was concentrated. The resultant was subjected to column chromatography with a mobile phase consisting of methanol and dichloromethane and then concentrated, so as to afford Compound 35. $^1$H NMR (400 MHz, CDCl$_3$) δ 4.23-4.19 (d, 8H), 3.74-3.70 (d, 4H), 2.87-2.84 (d, 4H), 2.52-2.41 (m, 12H), 2.31-2.25 (m, 2H), 2.08 (s, 3H), 1.76-1.14 (m, 68H), 0.91-0.83 (m, 18H).

Example 21 Synthesis of Compound 36

2-Ethylbutyric acid (1.5 eq) was dissolved in an appropriate amount of dichloromethane and stirred. EDC (1.5 eq), DMAP (0.5 eq) and triethylamine (1.0 eq) were added thereto, and the mixture was stirred at room temperature for 0.5 h. 6-Bromohexanol (1.0 eq) was added thereto, and the mixture was reacted at room temperature overnight. It was confirmed by TLC that the reaction of the raw materials was complete. Acetic acid was added to adjust pH to 6 to 7. The resultant was extracted several times, subjected to column chromatography with a mobile phase consisting of methanol and dichloromethane, and then concentrated, so as to afford a colorless and transparent liquid.

The above-mentioned resulting colorless and transparent liquid (4.8 eq) was dissolved in an appropriate amount of ethanol, potassium carbonate (4.8 eq) was added, N,N-bis(3-aminopropyl)methylamine (1.0 eq) was then added thereto, and the mixture was stirred at 75° C. overnight. The completion of the reaction of the raw materials was monitored by TLC, and the reaction solution was concentrated. The resultant was subjected to column chromatography with a mobile phase consisting of methanol and dichloromethane and then concentrated, so as to afford Compound 36. $^1$H NMR (400 MHz, CDCl$_3$) δ 4.15-4.10 (d, 8H), 2.94-2.87 (d, 8H), 2.51-2.47 (d, 8H), 2.42-2.39 (m, 4H), 2.22 (s, 3H), 1.85-1.23 (m, 52H), 0.95-0.90 (m, 24H).

Example 22 Synthesis of Compound 37

4-Methylvaleric acid (1.5 eq) was dissolved in an appropriate amount of dichloromethane and stirred. EDC (1.5 eq), DMAP (0.5 eq) and triethylamine (1.0 eq) were added thereto, and the mixture was stirred at room temperature for 0.5 h. 6-Bromohexanol (1.0 eq) was added thereto, and the mixture was reacted at room temperature overnight. It was confirmed by TLC that the reaction of the raw materials was complete. Acetic acid was added to adjust pH to 6 to 7. The resultant was extracted several times, subjected to column chromatography with a mobile phase consisting of methanol and dichloromethane, and then concentrated, so as to afford a colorless and transparent liquid.

The above-mentioned resulting colorless and transparent liquid (4.8 eq) was dissolved in an appropriate amount of ethanol, potassium carbonate (4.8 eq) was added, N,N-bis(3-aminopropyl)methylamine (1.0 eq) was then added thereto, and the mixture was stirred at 75° C. overnight. The completion of the reaction of the raw materials was monitored by TLC, and the reaction solution was concentrated. The resultant was subjected to column chromatography with a mobile phase consisting of methanol and dichloromethane and then concentrated, so as to afford Compound 37. $^1$H NMR (400 MHz, CDCl$_3$) δ 4.21-4.13 (d, 8H), 3.02-2.92 (d, 8H), 2.46-2.32 (m, 16H), 2.18 (s, 3H), 1.65-1.23 (m, 48H), 0.91-0.90 (m, 24H).

Example 23 Synthesis of Compound 38

2-Hexyldecanoic acid (1.5 eq) was dissolved in an appropriate amount of dichloromethane and stirred. EDC (1.5 eq), DMAP (0.5 eq) and triethylamine (1.0 eq) were added thereto, and the mixture was stirred at room temperature for 0.5 h. 2-Bromoethanol (1.0 eq) was added thereto, and the mixture was reacted at room temperature overnight. It was confirmed by TLC that the reaction of the raw materials was complete. Acetic acid was added to adjust pH to 6 to 7. The resultant was extracted several times, subjected to column chromatography with a mobile phase consisting of methanol and dichloromethane, and then concentrated, so as to afford a colorless and transparent liquid.

The above-mentioned resulting colorless and transparent liquid (2.1 eq) was dissolved in an appropriate amount of ethanol, potassium carbonate (2.4 eq) was added, N,N-bis(3-aminopropyl)methylamine (1.0 eq) was then added thereto, and the mixture was stirred at 75° C. overnight. The completion of the reaction of the raw materials was monitored by TLC, and the reaction solution was concentrated. The resultant was subjected to column chromatography with a mobile phase consisting of methanol and dichloromethane and concentrated, so as to afford a pale yellow oil.

The above-mentioned resulting oil (1.0 eq) was dissolved in an appropriate amount of methanol, isodecyl acrylate (2.5 eq) was added, and the mixture was stirred at 45° C. overnight. The completion of the reaction of the raw materials was monitored by TLC, and the reaction solution was concentrated. The resultant was subjected to column chromatography with a mobile phase consisting of methanol and dichloromethane and then concentrated, so as to afford Compound 38. $^1$H NMR (400 MHz, CDCl$_3$) δ 4.23-4.19 (m, 8H), 3.74-3.70 (d, 4H), 2.87-2.84 (d, 4H), 2.52-2.41 (m, 12H), 2.31-2.25 (m, 2H), 2.08 (s, 3H), 1.76-1.14 (m, 78H), 0.91-0.83 (m, 24H).

Example 24 Synthesis of Compound 39

2-Hexyldecanoic acid (1.5 eq) was dissolved in an appropriate amount of dichloromethane and stirred. EDC (1.5 eq), DMAP (0.5 eq) and triethylamine (1.0 eq) were added thereto, and the mixture was stirred at room temperature for 0.5 h. 4-Hydroxybutyl acrylate (1.0 eq) was added, and the mixture was reacted at room temperature overnight. It was confirmed by TLC that the reaction of the raw materials was complete. Acetic acid was added to adjust pH to 6 to 7. The resultant was extracted several times, subjected to column chromatography with a mobile phase consisting of methanol and dichloromethane, and then concentrated, so as to afford a colorless and transparent liquid.

The above-mentioned resulting oil (4.8 eq) was dissolved in an appropriate amount of methanol, N,N-bis(3-aminopropyl)methylamine (1.0 eq) was added, and the mixture was stirred at 45° C. overnight. The completion of the reaction of the raw materials was monitored by TLC, and the reaction solution was concentrated. The resultant was subjected to column chromatography with a mobile phase consisting of methanol and dichloromethane and then concentrated, so as to afford Compound 39. $^1$H NMR (400 MHz, CDCl$_3$) δ 4.12-4.01 (m, 16H), 2.76-2.64 (m, 12H), 2.47-2.27 (m, 16H), 2.01 (s, 3H), 1.75-1.14 (m, 116H), 0.88-0.85 (m, 24H).

Example 25 Synthesis of Compound 45

2-Butyloctanoic acid (1.5 eq) was dissolved in an appropriate amount of dichloromethane and stirred. EDC (1.5 eq), DMAP (0.5 eq) and triethylamine (1.0 eq) were added thereto, and the mixture was stirred at room temperature for 0.5 h. 4-Hydroxybutyl vinyl ether (1.0 eq) was added, and the mixture was reacted at room temperature overnight. It was confirmed by TLC that the reaction of the raw materials was complete. Acetic acid was added to adjust pH to 6 to 7. The resultant was extracted several times, subjected to column chromatography with a mobile phase consisting of methanol and dichloromethane, and then concentrated, so as to afford a colorless and transparent liquid.

The above-mentioned resulting oil (4.8 eq) was dissolved in an appropriate amount of methanol, N,N-bis(3-aminopropyl)methylamine (1.0 eq) was added, and the mixture was stirred at 45° C. overnight. The completion of the reaction of the raw materials was monitored by TLC, and the reaction solution was concentrated. The resultant was subjected to column chromatography with a mobile phase consisting of methanol and dichloromethane and then concentrated, so as to afford Compound 45. $^1$H NMR (400 MHz, CDCl$_3$) δ 4.12-4.01 (m, 8H), 3.62-3.58 (m, 8H), 3.48-3.45 (m, 8H), 2.47-2.35 (m, 16H), 2.31-2.27 (m, 4H), 2.18 (s, 3H), 1.75-1.14 (m, 84H), 0.91-0.88 (m, 24H).

Example 26

Compounds 1, 2, 17, 27 or 33 was each dissolved in the first solution with cholesterol, DOPE and PEG-DMG in a molar ratio of 35:46.5:16:2.5, and luciferase mRNA was dissolved in the second solution. Among them, the first solution was a mixed solution of 90% ethanol and 10% 50 mM citric acid buffered saline solution (pH 4.0), the second solution was 50 mM citric acid buffered saline solution (pH 4.0), and the two solutions had a volume ratio of 1:3. Microfluidics was utilized to quickly mix the two phases, and dialysis or tangential flow was utilized to replace the buffer environment with PBS (pH 7.4) and thus remove ethanol, so as to prepare and afford five kinds of LNP@mRNAs, respectively.

The particle size, PDI and encapsulation efficiency of each LNP@mRNA were determined, and the results were shown in Table 1. The results indicated that, LNP@mRNA prepared by Compound 1, 2, 27 or 33 and other three lipids had relatively small particle size, and LNP@mRNA prepared by Compound 1, 2, 17 or 33 and other three lipids had relatively high encapsulation efficiency.

TABLE 1

Particle size, PDI, and encapsulation efficiency of each LNP@mRNA

| Compound | Particle size (nm) | PDI | Encapsulation efficiency (%) |
|---|---|---|---|
| 1 | 95 | 0.14 | 96 |
| 2 | 84 | 0.20 | 86 |
| 17 | 184 | 0.19 | 96 |
| 27 | 90 | 0.21 | 57 |
| 33 | 86 | 0.11 | 96 |

Figure 2:
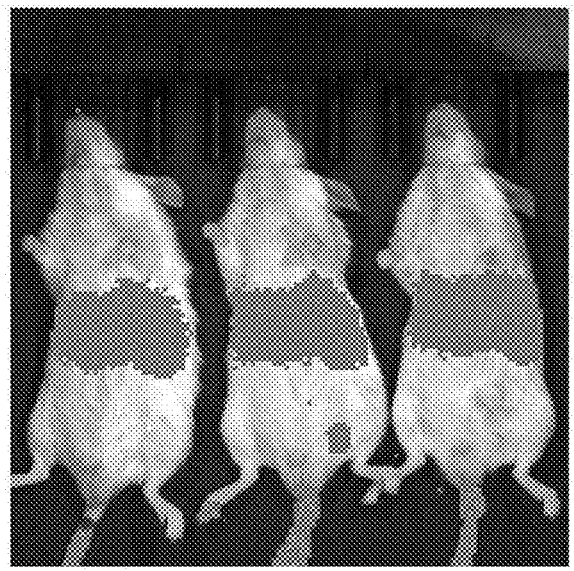
FIG. 2 shows the imaging results obtained 6 hours after the intravenous injection of LNP@mRNA prepared by Compound 2 and other three lipids in Example 26.
Figure 3:
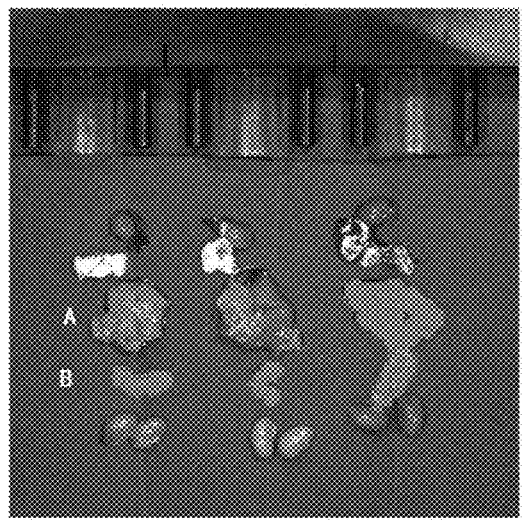
FIG. 3 shows the anatomical image obtained 6 hours after the intravenous injection of LNP@mRNA prepared by Compound 2 and other three lipids in Example 26.
Figure 4:
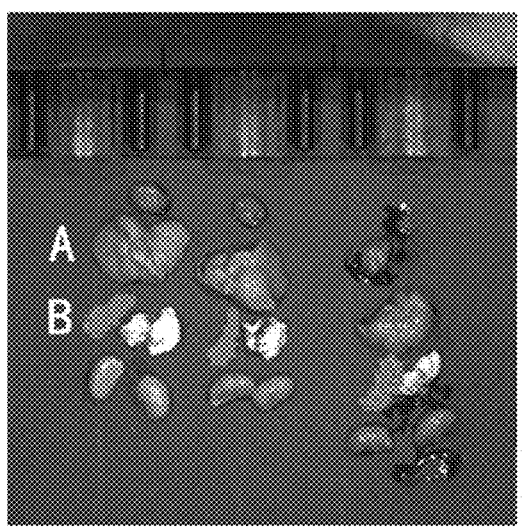
FIG. 4 shows the anatomical image obtained 6 hours after the intravenous injection of LNP@mRNA prepared by Compound 27 and other three lipids in Example 26.
Figure 5:
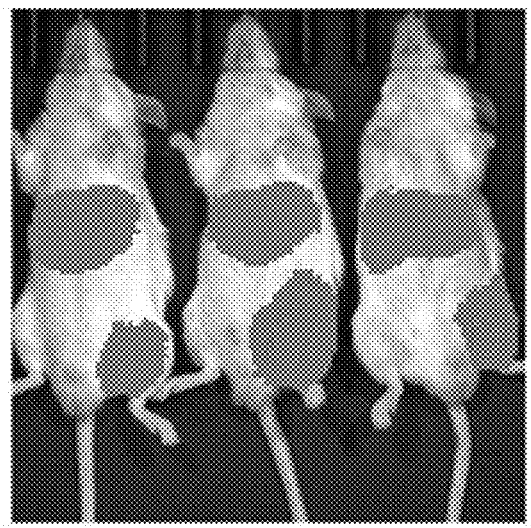
FIG. 5 shows the imaging results obtained 6 hours after the intravenous injection of LNP@mRNA prepared by Compound 33 and other three lipids in Example 26.
Figure 6:
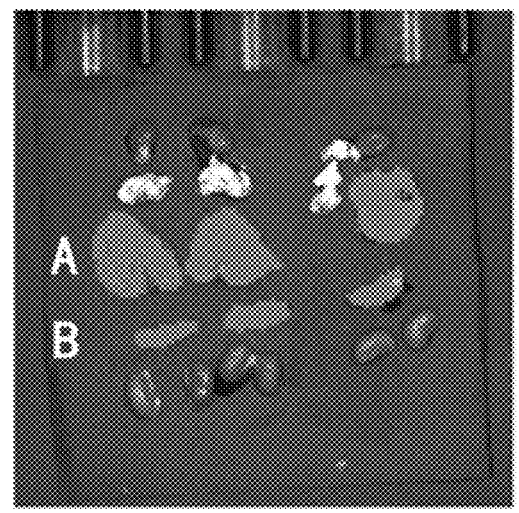
FIG. 6 shows the anatomical image obtained 6 hours after the intravenous injection of LNP@mRNA prepared by Compound 33 and other three lipids in Example 26.

The prepared LNP@mRNAs were each injected into mice via tail vein or muscle, and the fluorescence intensities and organ distribution in mice were determined 6 hours later. FIG. 1 showed the results obtained after the intramuscular injection of LNP@mRNA prepared by Compound 2 and other three lipids; FIG. 2 showed the results obtained after the tail vein injection of LNP@mRNA prepared by Compound 2 and other three lipids; FIG. 3 showed the anatomical image obtained after the intravenous injection of LNP@mRNA prepared by Compound 2 and other three lipids, and the results indicated that mRNA was mainly expressed in spleen (B of FIG. 3) while few mRNA was expressed in liver (A of FIG. 3); FIG. 4 showed the anatomical image obtained after the intravenous injection of LNP@mRNA prepared by Compound 27 and other three lipids, and the results indicated that mRNA was mainly expressed in spleen (B of FIG. 4) while few mRNA was expressed in liver (A of FIG. 4); FIG. 5 showed the results obtained after the tail vein injection of LNP@mRNA prepared by Compound 33 and other three lipid; and FIG. 6 showed the anatomical image obtained after the tail vein injection of LNP@mRNA prepared by Compound 33 and other three lipids, and the results indicated that mRNA was mainly expressed in liver (A of FIG. 6) while some mRNA was expressed in spleen (B of FIG. 6).

Figure 7:
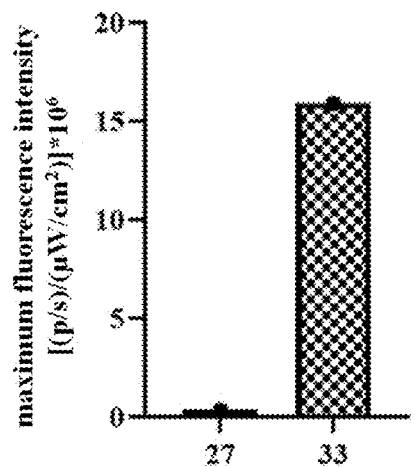
FIG. 7 shows the comparison diagram of maximum fluorescence intensities after the intramuscular injection of LNP@mRNAs prepared, in Example 26, respectively by Compound 27/33 and other three lipids.

FIG. 7 shows the comparison diagram of maximum fluorescence intensities after the intramuscular injection of LNP@mRNAs prepared respectively by Compound 27/33 and other three lipids, and the results indicated that, compared with the LNP@mRNA prepared by Compound 27 and other three lipids, the LNP@mRNA prepared by Compound 33 and other three lipids exhibited higher fluorescence intensity. Especially, the expression of LNP@mRNA prepared by Compound 33 and other three lipids was 46.9 times higher than that of LNP@mRNA prepared by Compound 27 and other three lipids (the maximum fluorescence intensities after the intramuscular injection of LNP@mRNAs prepared by Compound 27/33 and other three lipids are $3.39*10^5$ and $1.59*10^7$, respectively, indicating that the increase in the numbers of ester groups in compound greatly improved the expression of mRNA, and the effect is significantly improved.

Figure 8:
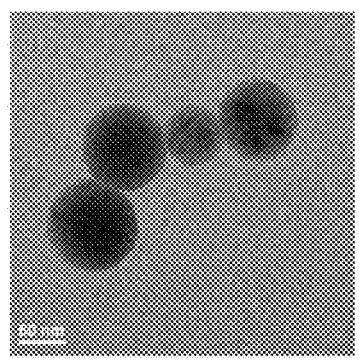
FIG. 8 shows the transmission electron microscopic image of LNP@mRNA prepared by Compound 2 and other three lipids in Example 26.

FIG. 8 showed the transmission electron microscopic image of LNP@mRNA prepared by Compound 2 and other three lipids.

Example 27

Compound 2 was dissolved in the first solution with cholesterol, DOPE, DSPC and PEG-DMG in each molar ratio as shown in Table 2, and luciferase mRNA was dissolved in the second solution. Among them, the first solution was an ethanol-water solution, the second solution was 50 mM citric acid buffered saline solution (pH 4.0), and the two solutions had a volume ratio of 1:3. Microfluidics was utilized to quickly mix the two phases, and dialysis or tangential flow was utilized to replace the buffer environment with PBS (pH 7.4) and thus remove ethanol, so as to prepare and afford LNP@mRNA.

TABLE 2

Dissolution ratio of Compound 2 and other three lipids in the first solution

| Sample name | Compound 2 | cholesterol | DSPC | DOPE | PEG-DMG | First solution (v/v) Ethanol | Water |
|---|---|---|---|---|---|---|---|
| Ratio 1 | 35 | 46.5 | 0 | 16 | 2.5 | 100 | 0 |
| Ratio 2 | 35 | 46.5 | 0 | 16 | 2.5 | 90 | 10 |
| Ratio 3 | 50 | 38.5 | 0 | 10 | 1.5 | 100 | 0 |
| Ratio 4 | 50 | 38.5 | 0 | 10 | 1.5 | 90 | 10 |
| Ratio 5 | 50 | 38.5 | 10 | 0 | 1.5 | 100 | 0 |

The particle size, PDI and encapsulation efficiency of each of the above-mentioned LNP@mRNAs were determined, and the results were successively shown in Table 3.

TABLE 3

Particle size, PDI and encapsulation efficiency of each LNP@mRNA

| Sample name | Particle size (nm) | PDI | Encapsulation efficiency (%) |
|---|---|---|---|
| Ratio 1 | 93 | 0.36 | 82 |
| Ratio 2 | 77 | 0.14 | 70 |
| Ratio 3 | 58 | 0.15 | 85 |
| Ratio 4 | 76 | 0.32 | 80 |
| Ratio 5 | 139 | 0.17 | 69 |

Figure 9:
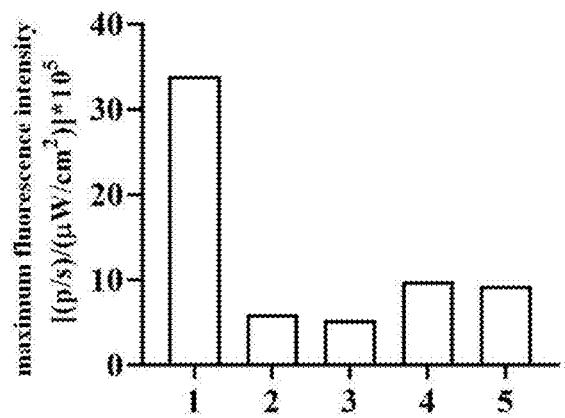
FIG. 9 shows the maximum fluorescence intensities obtained in test mice 6 hours after the intramuscular injection of LNP@mRNAs prepared by Compound 2 and several other lipids in different ratios in Example 27.

The prepared mRNA@LNPs were each injected into mice via intramuscular injection, and the fluorescence intensities and organ distribution in mice were determined 6 hours later. FIG. 9 showed the maximum fluorescence intensities obtained in test mice 6 hours after the intramuscular injection of LNP@mRNAs prepared by Compound 2 and several other lipids in different ratios, and the results indicated that mRNA@LNP prepared in Ratio 1 showed the highest expression in mice.

Changes of Zeta potential of LNP@mRNAs prepared in different molar ratios were determined at different pH, and the results were as shown in Table 4 below. It could be seen from Table 4 that, LNP prepared by such compound could exhibit different charge at different pH, that is, it was positively charged under acidic conditions and could attract a negatively charged nucleic acid drug, and it would exhibit electrical neutrality or be negatively charged under neutral conditions and would not interact with negatively charged cell membrane in vivo, thereby avoiding the occurrence of cytotoxicity.

TABLE 4

Changes of Zeta potential of LNP@mRNAs at different pH

| Zeta (mV) | pH 4.0 | pH 7.4 | pH 10.0 |
|---|---|---|---|
| 1 | 10.8 | −1.1 | −41.8 |
| 2 | 9.05 | −4.29 | −39.4 |
| 3 | 8.42 | −9.63 | −32.5 |
| 4 | 9.35 | −10.6 | −33.3 |
| 5 | 8.19 | −14.4 | −44.1 |

Example 28

Compound 2 was dissolved in the first solution with DOTAP, cholesterol, DSPC and PEG-DMG in a molar ratio of 30:20:38.5:10:1.5, and luciferase mRNA was dissolved in the second solution. Among them, the first solution was ethanol, the second solution was 50 mM citric acid buffered saline solution (pH 4.0), and the two solutions had a volume ratio of 1:3. Microfluidics was utilized to quickly mix the two phases, and dialysis or tangential flow was utilized to replace the buffer environment with PBS (pH 7.4), so as to prepare and afford LNP@mRNA. Sucrose was added as a cryopreservation protective agent, and a nucleic acid lipid nanoparticle pharmaceutical preparation was obtained.

Example 29

Compound 34 was dissolved in the first solution with DOTAP, phosphatidylserine, cholesterol, DSPC and PEG-DMG (15 mg in total) in a molar ratio of 20:25:15:25:5:10, and luciferase mRNA (5 mg) was dissolved in the second solution. Among them, the first solution was ethanol, the second solution was 50 mM citric acid buffered saline solution (pH 4.0), and the two solutions had a volume ratio of 1:3. Microfluidics was utilized to quickly mix the two phases, and dialysis or tangential flow was utilized to replace the buffer environment with PBS (pH 7.4), so as to prepare and afford LNP@mRNA. Sucrose was added as a cryopreservation protective agent, and a nucleic acid lipid nanoparticle pharmaceutical preparation was obtained.

Example 30

Compound 37 was dissolved in the first solution with Dlin-KC2-DMA, DOPG, cholesterol, DSPC and Tween-80 (30 mg in total) in a molar ratio of 15:5:3:51.5:25:0.5, and luciferase mRNA (1 mg) was dissolved in the second solution. Among them, the first solution was ethanol, the second solution was 50 mM citric acid buffered saline solution (pH 4.0), and the two solutions had a volume ratio of 1:3. Microfluidics was utilized to quickly mix the two phases, and dialysis or tangential flow was utilized to replace the buffer environment with PBS (pH 7.4), so as to prepare and afford LNP@mRNA. Sucrose was added as a cryopreservation protective agent, and a nucleic acid lipid nanoparticle pharmaceutical preparation was obtained.

It should be noted that, although the technical solutions of the present disclosure have been described by means of specific embodiments, those skilled in the art can understand that the present disclosure should not be limited thereto. Each embodiment of the present disclosure have been described above, and the above-mentioned description is exemplary and non-exhaustive, and is not limited to each disclosed embodiment. Without departing from the scope and spirit of each embodiment as described, many modifications and changes are obvious to those of ordinary skill in the art. The selection of terms used herein aims at optimally explaining the principle, practical application or technical improvements to the arts on market of each embodiment, or enabling other ordinary skilled in the art to understand each embodiment disclosed herein.

What is claimed is:

1. A compound of formula (I-1-1), or a pharmaceutically acceptable salt, a stereoisomer, a tautomer, a solvate, a chelate, a non-covalent complex or a prodrug thereof,

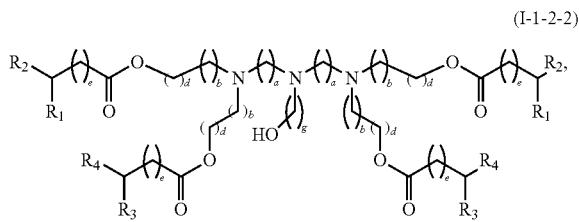

(I-1-2-2)

wherein
each of A is independently one or more substituents selected from the group consisting of —O(C═O)—, —(C═O)O—, —C(═O)S—, —SC(═O)—, —NHC (═O)—, and —C(═O)NH—;
each of $R_1$, $R_2$, $R_3$ and $R_4$ is independently an alkyl group containing 1 to 16 carbon atoms;
$R_5$ is a $C_{1-12}$ alkyl group; and
each of a, b, d and e is independently any integer ranging from 0 to 14.

2. A lipid vector, comprising the compound or the pharmaceutically acceptable salt, the stereoisomer, the tautomer, the solvate, the chelate, the non-covalent complex or the prodrug thereof according to claim 1; wherein
the lipid vector comprises a first lipid compound and a second lipid compound, wherein the first lipid compound comprises the compound or the pharmaceutically acceptable salt, the stereoisomer, the tautomer, the solvate, the chelate, the non-covalent complex or the prodrug thereof and a second cationic lipid, the second lipid compound comprises at least one selected from the group consisting of an anionic lipid, a neutral lipid, a sterol and an amphiphilic lipid;
wherein the second cationic lipid is at least one selected from the group consisting of DLinDMA, DODMA, DLin-MC2-MPZ, DLin-KC2-DMA, DOTAP, C12-200, DC-Chol and DOTMA;
the anionic lipid is at least one selected from the group consisting of phosphatidylserine, phosphatidylinositol, phosphatidic acid, phosphatidylglycerol, DOPG and dimyristoylphosphatidylglycerol;
the neutral lipid is at least one selected from the group consisting of DOPE, DSPC, DPPC, DOPC, DPPG, POPC, POPE, DPPE, DMPE, DSPE and SOPE, or a lipid obtained by modifying the above neutral lipid with an anionic or cationic modifying group; and
the amphiphilic lipid is at least one selected from the group consisting of PEG-DMG, PEG-c-DMG, PEG-C14, PEG-c-DMA, PEG-DSPE, PEG-PE, a PEG-modified ceramide, a PEG-modified dialkylamine, a PEG-modified diacylglycerol, polysorbate 20, polysorbate 80, PEG-DPG, PEG-s-DMG, DAA, PEG-c-DOMG and GalNAc-PEG-DSG.

3. The lipid vector according to claim 2, wherein a molar ratio of the first lipid compound, the anionic lipid, the neutral lipid, the sterol and the amphiphilic lipid in the lipid vector is (20 to 65):(0 to 20):(5 to 25):(25 to 55):(0.3 to 15).

4. A nucleic acid lipid nanoparticle composition, comprising the compound or the pharmaceutically acceptable salt, the stereoisomer, the tautomer, the solvate, the chelate, the non-covalent complex or the prodrug thereof according to claim 1, and a nucleic acid drug;
wherein the nucleic acid drug is at least one selected from the group consisting of a DNA, an siRNA, an mRNA, a dsRNA, an antisense nucleic acid, an microRNA, an antisense microRNA, antagomir, an microRNA inhibitor, an microRNA agonist and an immunostimulatory nucleic acid; or
wherein a mass ratio of the nucleic acid drug to the compound or the pharmaceutically acceptable salt, the stereoisomer, the tautomer, the solvate, the chelate, the non-covalent complex or the prodrug thereof is 1:(3 to 40).

5. A pharmaceutical preparation, comprising the compound or the pharmaceutically acceptable salt, the stereoisomer, the tautomer, the solvate, the chelate, the non-covalent complex or the prodrug thereof according to claim 1, a nucleic acid drug, and a pharmaceutically acceptable excipient, carrier and diluent;
wherein the pharmaceutical preparation has a particle size of 30 to 500 nm; or
wherein an encapsulation efficiency of the nucleic acid drug in the pharmaceutical preparation is higher than 50%.

6. A nucleic acid lipid nanoparticle composition, comprising the lipid vector according to claim 2, and a nucleic acid drug;
wherein the nucleic acid drug is at least one selected from the group consisting of a DNA, an siRNA, an mRNA, a dsRNA, an antisense nucleic acid, an microRNA, an antisense microRNA, antagomir, an microRNA inhibitor, an microRNA agonist and an immunostimulatory nucleic acid; or
wherein a mass ratio of the nucleic acid drug to the lipid vector is 1:(3 to 40).

7. A pharmaceutical preparation, comprising the lipid vector according to claim 2, a nucleic acid drug, and a pharmaceutically acceptable excipient, carrier and diluent;
wherein the pharmaceutical preparation has a particle size of 30 to 500 nm; or
wherein an encapsulation efficiency of the nucleic acid drug in the pharmaceutical preparation is higher than 50%.

8. A pharmaceutical preparation, comprising the nucleic acid lipid nanoparticle composition according to claim 4, and a pharmaceutically acceptable excipient, carrier and diluent;
wherein the pharmaceutical preparation has a particle size of 30 to 500 nm; or
wherein an encapsulation efficiency of the nucleic acid drug in the pharmaceutical preparation is higher than 50%.

9. The following compounds, or pharmaceutically acceptable salts, stereoisomers, tautomers, solvates, chelates, non-covalent complexes or prodrugs thereof,

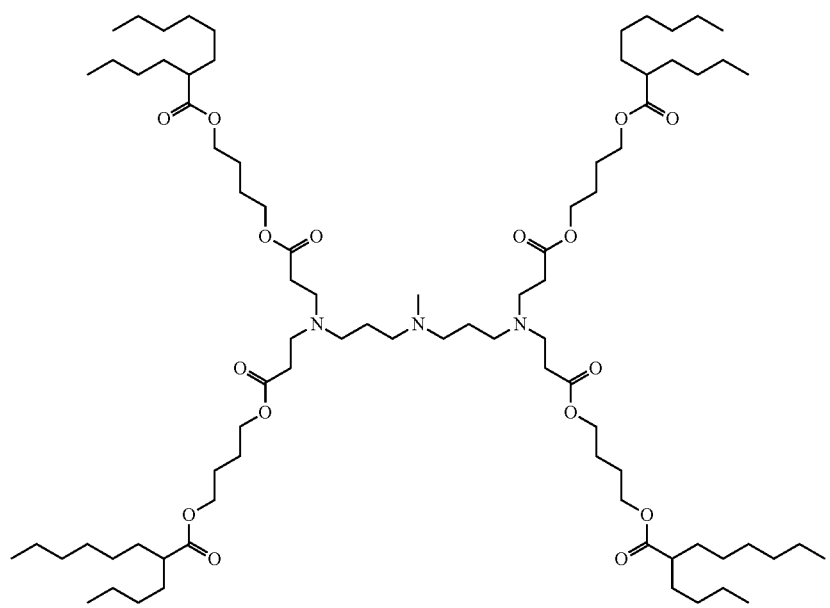

33

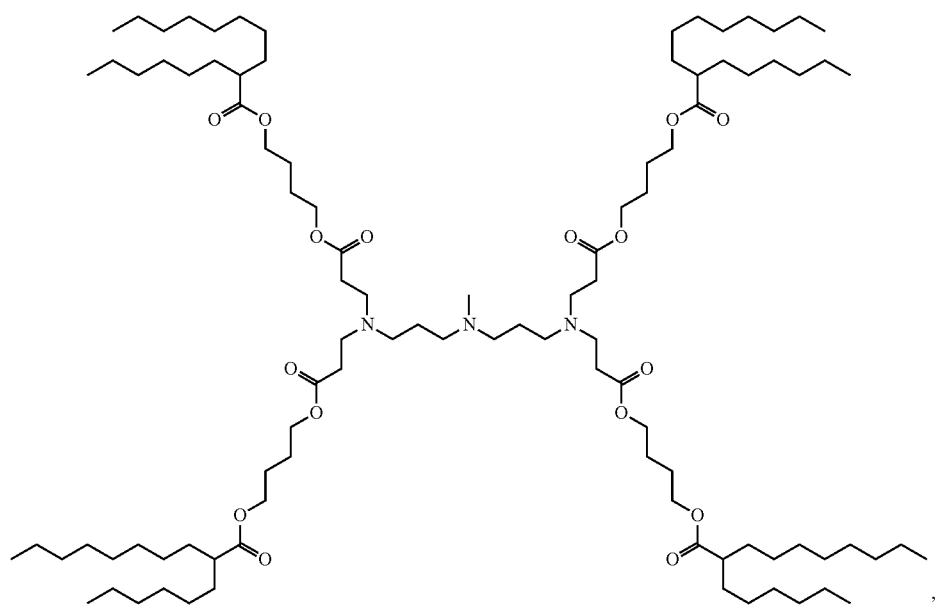
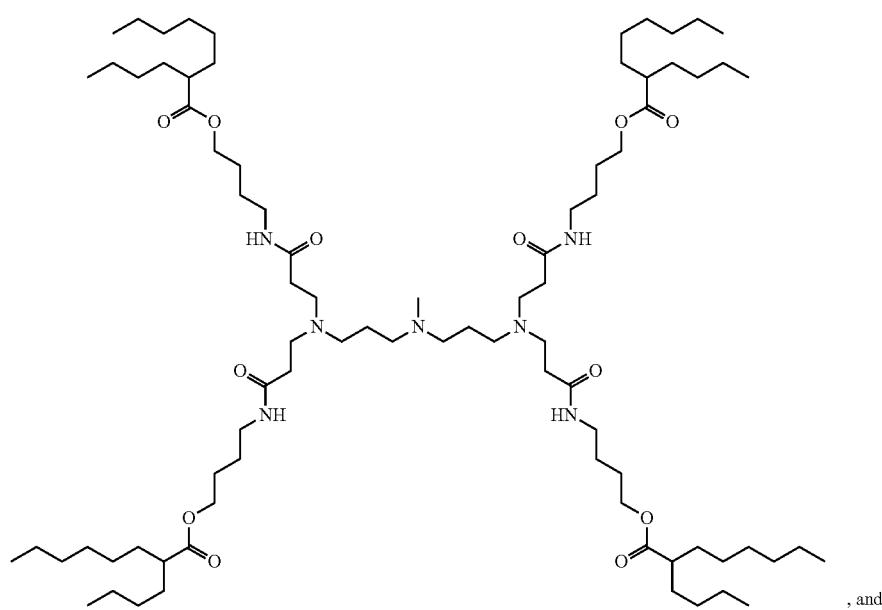
, and

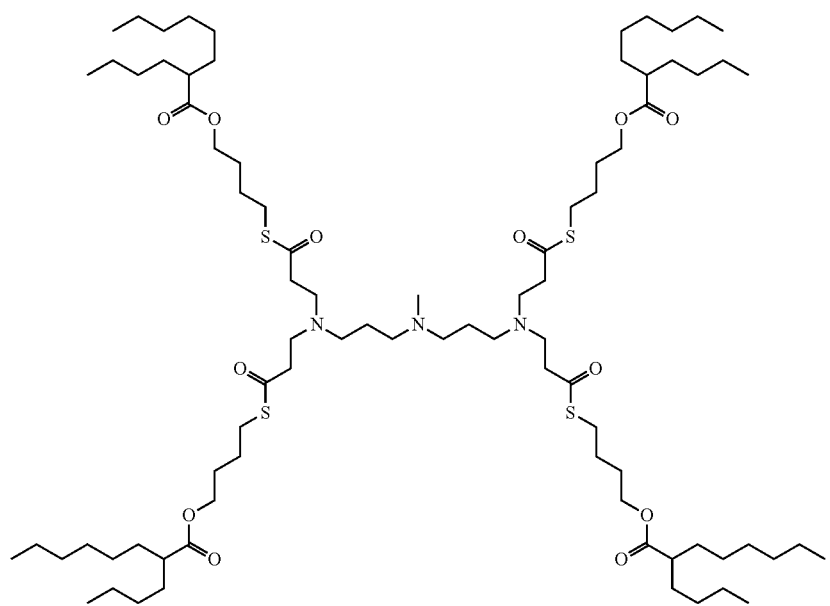
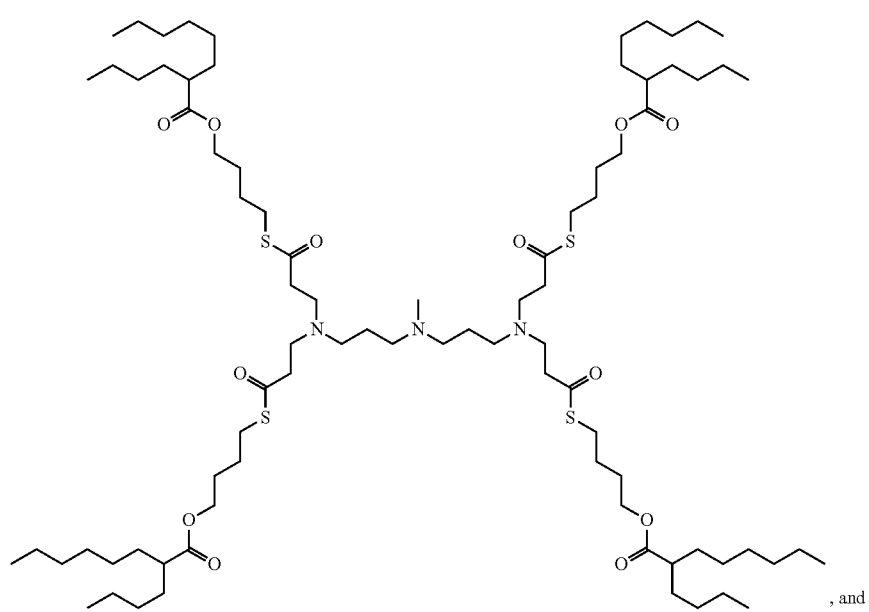
, and

-continued

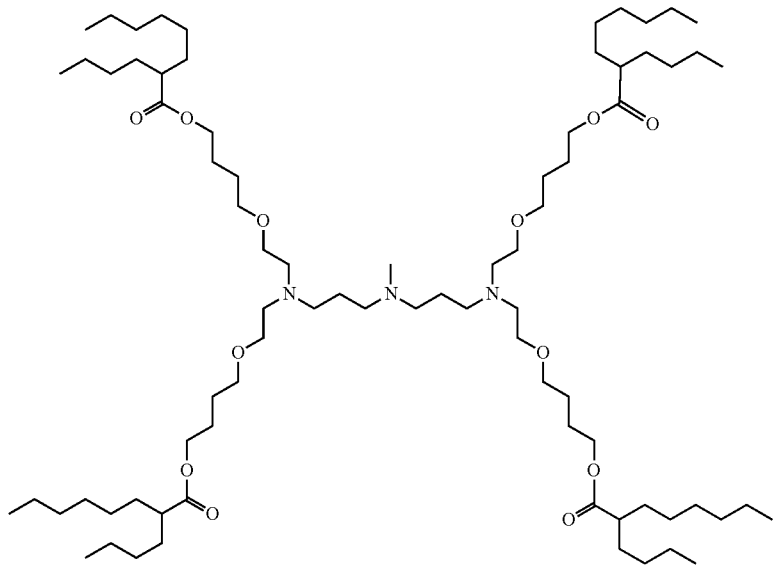
45

10. A lipid vector, comprising the compound or the pharmaceutically acceptable salt, the stereoisomer, the tautomer, the solvate, the chelate, the non-covalent complex or the prodrug thereof according to claim 9, wherein
the lipid vector comprises a first lipid compound and a second lipid compound, wherein the first lipid compound comprises the compound or the pharmaceutically acceptable salt, the stereoisomer, the tautomer, the solvate, the chelate, the non-covalent complex or the prodrug thereof and a second cationic lipid, the second lipid compound comprises at least one selected from the group consisting of an anionic lipid, a neutral lipid, a sterol and an amphiphilic lipid;
wherein the second cationic lipid is at least one selected from the group consisting of DLinDMA, DODMA, DLin-MC2-MPZ, DLin-KC2-DMA, DOTAP, C12-200, DC-Chol and DOTMA;
the anionic lipid is at least one selected from the group consisting of phosphatidylserine, phosphatidylinositol, phosphatidic acid, phosphatidylglycerol, DOPG and dimyristoylphosphatidylglycerol;
the neutral lipid is at least one selected from the group consisting of DOPE, DSPC, DPPC, DOPC, DPPG, POPC, POPE, DPPE, DMPE, DSPE and SOPE, or a lipid obtained by modifying the above neutral lipid with an anionic or cationic modifying group; and
the amphiphilic lipid is at least one selected from the group consisting of PEG-DMG, PEG-c-DMG, PEG-C14, PEG-c-DMA, PEG-DSPE, PEG-PE, a PEG-modified ceramide, a PEG-modified dialkylamine, a PEG-modified diacylglycerol, polysorbate 20, polysorbate 80, PEG-DPG, PEG-s-DMG, DAA, PEG-c-DOMG and GalNAc-PEG-DSG.

11. The lipid vector according to claim 10, wherein a molar ratio of the first lipid compound, the anionic lipid, the neutral lipid, the sterol and the amphiphilic lipid in the lipid vector is (20 to 65):(0 to 20):(5 to 25):(25 to 55):(0.3 to 15).

12. A nucleic acid lipid nanoparticle composition, comprising the compound or the pharmaceutically acceptable salt, the stereoisomer, the tautomer, the solvate, the chelate, the non-covalent complex or the prodrug thereof according to claim 9, and a nucleic acid drug;
wherein the nucleic acid drug is at least one selected from the group consisting of a DNA, an siRNA, an mRNA, a dsRNA, an antisense nucleic acid, an microRNA, an antisense microRNA, antagomir, an microRNA inhibitor, an microRNA agonist and an immunostimulatory nucleic acid; or
wherein a mass ratio of the nucleic acid drug to the compound or the pharmaceutically acceptable salt, the stereoisomer, the tautomer, the solvate, the chelate, the non-covalent complex or the prodrug thereof is 1:(3 to 40).

13. A pharmaceutical preparation, comprising the compound or the pharmaceutically acceptable salt, the stereoisomer, the tautomer, the solvate, the chelate, the non-covalent complex or the prodrug thereof according to claim 9, a nucleic acid drug, and a pharmaceutically acceptable excipient, carrier and diluent;
wherein the pharmaceutical preparation has a particle size of 30 to 500 nm; or
wherein an encapsulation efficiency of the nucleic acid drug in the pharmaceutical preparation is higher than 50%.

14. A nucleic acid lipid nanoparticle composition, comprising the lipid vector according to claim 10, and a nucleic acid drug;
wherein the nucleic acid drug is at least one selected from the group consisting of a DNA, an siRNA, an mRNA, a dsRNA, an antisense nucleic acid, an microRNA, an antisense microRNA, antagomir, an microRNA inhibitor, an microRNA agonist and an immunostimulatory nucleic acid; or
wherein a mass ratio of the nucleic acid drug to the lipid vector is 1:(3 to 40).

15. A pharmaceutical preparation, comprising the lipid vector according to claim 2, a nucleic acid drug, and a pharmaceutically acceptable excipient, carrier and diluent;
wherein the pharmaceutical preparation has a particle size of 30 to 500 nm; or wherein an encapsulation efficiency of the nucleic acid drug in the pharmaceutical preparation is higher than 50%.

16. A pharmaceutical preparation, comprising the nucleic acid lipid nanoparticle composition according to claim 12, and a pharmaceutically acceptable excipient, carrier and diluent;

wherein the pharmaceutical preparation has a particle size of 30 to 500 nm; or wherein an encapsulation efficiency of the nucleic acid drug in the pharmaceutical preparation is higher than 50%.

\* \* \* \* \*